(12) United States Patent
Sali et al.

(10) Patent No.: US 7,813,541 B2
(45) Date of Patent: Oct. 12, 2010

(54) METHOD AND APPARATUS FOR DETECTING DEFECTS IN WAFERS

(75) Inventors: Erez Sali, Savion (IL); Tomer Yanir, Yehud (IL); Mark Wagner, Rehovot (IL); Noam Dotan, Givatayim (IL); Yuval Dorfan, Ra'anana (IL); Ran Zaslavsky, Kfar Saba (IL)

(73) Assignee: Applied Materials South East Asia Pte. Ltd., Singapore (SG)

( * ) Notice: Subject to any disclaimer, the term of this patent is extended or adjusted under 35 U.S.C. 154(b) by 1250 days.

(21) Appl. No.: 11/069,712

(22) Filed: Feb. 28, 2005

(65) Prior Publication Data

US 2006/0193507 A1 Aug. 31, 2006

(51) Int. Cl.
*G06K 9/00* (2006.01)
(52) U.S. Cl. .................. 382/144; 382/145; 382/151
(58) Field of Classification Search .......... 382/145, 382/144, 151, 173, 218, 236, 260, 294; 356/237.2, 356/237.4
See application file for complete search history.

(56) References Cited

U.S. PATENT DOCUMENTS

| | | |
|---|---|---|
| 3,220,331 A | 11/1965 | Evans et al. |
| 3,598,467 A | 8/1971 | Pearson |
| 3,790,280 A | 2/1974 | Heinz et al. |
| 4,011,403 A | 3/1977 | Epstein et al. |
| 4,247,203 A | 1/1981 | Levy et al. |
| 4,347,001 A | 8/1982 | Levy et al. |
| 4,360,372 A | 11/1982 | Maciejko |
| 4,378,159 A | 3/1983 | Galbraith |
| 4,462,662 A | 7/1984 | Lama |
| 4,486,776 A | 12/1984 | Yoshida |
| 4,532,650 A | 7/1985 | Wihl et al. |
| 4,556,317 A | 12/1985 | Sandland et al. |
| 4,579,455 A | 4/1986 | Levy et al. |
| 4,588,293 A | 5/1986 | Axelrod |
| 4,589,736 A | 5/1986 | Harrigan et al. |
| 4,597,665 A | 7/1986 | Galbraith et al. |
| 4,601,576 A | 7/1986 | Galbraith |

(Continued)

FOREIGN PATENT DOCUMENTS

EP 0 959 378 11/1999

(Continued)

OTHER PUBLICATIONS

"Speckle Reduction" by T.S. McKecknie, pp. 123-170 in Topics in Applied Physics, vol. 9, Laser Speckle and Related Phenomena, edited by J.C. Dainty, Springer Verlag 1984.

(Continued)

*Primary Examiner*—Daniel G Mariam
*Assistant Examiner*—Aklilu k Woldemariam
(74) *Attorney, Agent, or Firm*—Sonnenschein Nath & Rosenthal LLP

(57) ABSTRACT

A method for inspecting a wafer including a multiplicity of dies, the method including dividing an image of at least a portion of the wafer into a plurality of sub-images each representing a sub-portion of the wafer and selecting at least one defect candidate within each sub-image by comparing each sub-image to a corresponding sub-image of a reference including a representation, which is assumed to be faultless, of the portion of the wafer.

15 Claims, 25 Drawing Sheets

U.S. PATENT DOCUMENTS

| | | | |
|---|---|---|---|
| 4,618,938 A | 10/1986 | Sandland | |
| 4,619,507 A | 10/1986 | Shibuya et al. | |
| 4,639,587 A | 1/1987 | Chadwick et al. | |
| 4,644,172 A | 2/1987 | Sandland et al. | |
| 4,734,923 A | 3/1988 | Frankel et al. | |
| 4,760,265 A | 7/1988 | Yoshida et al. | |
| 4,763,975 A | 8/1988 | Scifres et al. | |
| 4,766,324 A | 8/1988 | Saadat et al. | |
| 4,806,774 A | 2/1989 | Lin et al. | |
| 4,845,558 A | 7/1989 | Tsai et al. | |
| 4,877,326 A | 10/1989 | Chadwick et al. | |
| 4,898,471 A | 2/1990 | Vaught et al. | |
| 4,929,081 A | 5/1990 | Yamamoto et al. | |
| 4,964,692 A | 10/1990 | Prescott | |
| 4,967,095 A | 10/1990 | Berger et al. | |
| 4,969,198 A | 11/1990 | Batchelder et al. | |
| 5,008,743 A | 4/1991 | Katzir et al. | |
| 5,029,975 A | 7/1991 | Pease | |
| 5,038,048 A * | 8/1991 | Maeda et al. | 250/559.41 |
| 5,046,847 A | 9/1991 | Nakata et al. | |
| 5,056,765 A | 10/1991 | Branstater | |
| 5,058,982 A | 10/1991 | Katzir | |
| 5,076,692 A | 12/1991 | Neukermans et al. | |
| 5,112,129 A | 5/1992 | Davidson et al. | |
| 5,153,668 A | 10/1992 | Katzir et al. | |
| 5,172,000 A | 12/1992 | Scheff et al. | |
| 5,177,559 A | 1/1993 | Batchelder et al. | |
| 5,185,812 A | 2/1993 | Yamashita et al. | |
| 5,194,959 A | 3/1993 | Kaneko et al. | |
| 5,233,460 A | 8/1993 | Partlo et al. | |
| 5,264,912 A | 11/1993 | Vaught et al. | |
| 5,267,017 A | 11/1993 | Uritsky et al. | |
| 5,276,498 A | 1/1994 | Galbraith et al. | |
| 5,302,999 A | 4/1994 | Oshida et al. | |
| 5,381,004 A | 1/1995 | Uritsky et al. | |
| 5,422,724 A | 6/1995 | Kinney et al. | |
| 5,469,274 A * | 11/1995 | Iwasaki et al. | 358/450 |
| 5,471,066 A | 11/1995 | Hagiwara | |
| 5,471,341 A | 11/1995 | Warde et al. | |
| 5,506,676 A | 4/1996 | Hendler et al. | |
| 5,537,669 A | 7/1996 | Evans et al. | |
| 5,583,632 A | 12/1996 | Haga | |
| 5,586,058 A | 12/1996 | Aloni et al. | |
| 5,589,862 A | 12/1996 | Ujita et al. | |
| 5,604,585 A | 2/1997 | Johnson et al. | |
| 5,608,155 A | 3/1997 | Ye et al. | |
| 5,617,203 A | 4/1997 | Kobayashi et al. | |
| 5,619,429 A | 4/1997 | Aloni et al. | |
| 5,619,588 A | 4/1997 | Yolles et al. | |
| 5,629,768 A | 5/1997 | Hagiwara | |
| 5,659,172 A | 8/1997 | Wagner et al. | |
| 5,659,390 A | 8/1997 | Danko | |
| 5,689,592 A | 11/1997 | Ericsson et al. | |
| 5,694,481 A | 12/1997 | Lam et al. | |
| 5,699,447 A | 12/1997 | Alumot et al. | |
| 5,784,189 A | 7/1998 | Bozler et al. | |
| 5,797,317 A | 8/1998 | Lahat et al. | |
| 5,798,829 A | 8/1998 | Vaez-Iravani | |
| 4,805,123 A | 10/1998 | Specht et al. | |
| 5,822,055 A | 10/1998 | Tsai et al. | |
| 5,825,482 A | 10/1998 | Nikoonahad et al. | |
| 5,859,698 A | 1/1999 | Chau | |
| 5,864,394 A | 1/1999 | Jordan, III et al. | |
| 5,872,862 A * | 2/1999 | Okubo et al. | 382/151 |
| 5,883,710 A | 3/1999 | Nikoonahad et al. | |
| 5,892,579 A | 4/1999 | Elyasaf et al. | |
| 5,907,628 A | 5/1999 | Yolles et al. | |
| 5,912,735 A | 6/1999 | Xu | |
| 5,917,588 A | 6/1999 | Addiego | |
| 5,939,647 A | 8/1999 | Chinn et al. | |
| 5,970,168 A | 10/1999 | Montesanto et al. | |
| 5,982,921 A | 11/1999 | Alumot et al. | |
| 5,991,699 A | 11/1999 | Kulkarni et al. | |
| 5,995,665 A * | 11/1999 | Maeda | 382/232 |
| 6,020,957 A | 2/2000 | Rosengaus et al. | |
| 6,021,214 A | 2/2000 | Evans et al. | |
| 6,064,517 A | 5/2000 | Chuang et al. | |
| 6,075,375 A | 6/2000 | Burkhart et al. | |
| 6,078,386 A | 6/2000 | Tsai et al. | |
| 6,081,325 A | 6/2000 | Leslie et al. | |
| 6,081,381 A | 6/2000 | Shalapenok et al. | |
| 6,099,596 A | 8/2000 | Li et al. | |
| 6,122,046 A | 9/2000 | Almogy | |
| 6,124,924 A | 9/2000 | Feldman et al. | |
| 6,169,282 B1 | 1/2001 | Maeda et al. | |
| 6,172,349 B1 | 1/2001 | Katz et al. | |
| 6,175,645 B1 | 1/2001 | Elyasaf et al. | |
| 6,175,646 B1 | 1/2001 | Schemmel et al. | |
| 6,178,257 B1 | 1/2001 | Alumot et al. | |
| 6,201,601 B1 | 3/2001 | Vaez-Irvani et al. | |
| 6,208,411 B1 | 3/2001 | Vaez-Iravani | |
| 6,208,750 B1 | 3/2001 | Tsadka | |
| 6,215,551 B1 | 4/2001 | Nikoonahad et al. | |
| 6,226,116 B1 | 5/2001 | Dowe et al. | |
| 6,236,454 B1 | 5/2001 | Almogy | |
| 6,246,822 B1 | 6/2001 | Kim et al. | |
| 6,250,778 B1 | 6/2001 | Doumuki | |
| 6,256,093 B1 | 7/2001 | Ravid et al. | |
| 6,267,005 B1 | 7/2001 | Samsavar et al. | |
| 6,268,093 B1 | 7/2001 | Kenan et al. | |
| 6,268,916 B1 | 7/2001 | Lee et al. | |
| 6,271,916 B1 | 8/2001 | Marxer et al. | |
| 6,274,878 B1 | 8/2001 | Li et al. | |
| 6,282,309 B1 | 8/2001 | Emery | |
| 6,288,780 B1 | 9/2001 | Fairley et al. | |
| 6,317,514 B1 | 11/2001 | Reinhorn et al. | |
| 6,324,298 B1 | 11/2001 | O'Dell et al. | |
| 6,347,173 B1 | 2/2002 | Suganuma et al. | |
| 6,360,005 B1 | 3/2002 | Aloni et al. | |
| 6,361,910 B1 | 3/2002 | Sarig et al. | |
| 6,366,315 B1 | 4/2002 | Drescher | |
| 6,369,888 B1 | 4/2002 | Karpol et al. | |
| 6,392,747 B1 | 5/2002 | Allen et al. | |
| 6,456,420 B1 | 9/2002 | Goodwin-Johansson | |
| 6,456,769 B1 | 9/2002 | Furusawa et al. | |
| 6,504,948 B1 | 1/2003 | Schemmel et al. | |
| 6,536,882 B1 | 3/2003 | Hawkins et al. | |
| 6,628,681 B2 | 9/2003 | Kubota et al. | |
| 6,657,157 B1 | 12/2003 | Altman et al. | |
| 6,686,602 B2 | 2/2004 | Some | |
| 6,686,994 B2 | 2/2004 | Wilke et al. | |
| 6,686,995 B2 | 2/2004 | Wilk et al. | |
| 6,693,664 B2 | 2/2004 | Neumann | |
| 6,710,868 B2 | 3/2004 | Guetta | |
| 6,724,473 B2 | 4/2004 | Leong et al. | |
| 6,774,991 B1 | 8/2004 | Danko | |
| 6,781,688 B2 | 8/2004 | Kren et al. | |
| 6,796,699 B2 | 9/2004 | Birk et al. | |
| 6,798,605 B2 | 9/2004 | Karpol et al. | |
| 6,816,249 B2 | 11/2004 | Fairley et al. | |
| 6,818,459 B2 | 11/2004 | Wack | |
| 6,892,013 B2 | 5/2005 | Furman et al. | |
| 6,895,149 B1 | 5/2005 | Jacob et al. | |
| 6,906,794 B2 * | 6/2005 | Tsuji | 356/237.4 |
| 6,919,958 B2 | 7/2005 | Stanke et al. | |
| 6,941,007 B1 * | 9/2005 | Do | 382/145 |
| 6,947,587 B1 * | 9/2005 | Maeda et al. | 382/149 |
| 7,102,743 B2 * | 9/2006 | Tsuji et al. | 356/237.2 |
| 7,155,052 B2 | 12/2006 | Geshel et al. | |
| 7,254,281 B2 | 8/2007 | Slavin | |
| 7,265,900 B2 | 9/2007 | Korngut | |
| 7,525,659 B2 | 4/2009 | Furman et al. | |
| 7,630,069 B2 | 12/2009 | Naftali | |
| 2002/0037099 A1 | 3/2002 | Ogawa et al. | |

| | | | |
|---|---|---|---|
| 2002/0054291 | A1 | 5/2002 | Tsai et al. |
| 2002/0067478 | A1 | 6/2002 | Karpol et al. |
| 2002/0191066 | A1 | 12/2002 | Bouchard et al. |
| 2003/0048957 | A1 | 3/2003 | Dai et al. |
| 2003/0184739 | A1 | 10/2003 | Wilk et al. |
| 2003/0202178 | A1* | 10/2003 | Tsuji et al. ............... 356/237.2 |
| 2003/0227618 | A1 | 12/2003 | Some |
| 2004/0057611 | A1 | 3/2004 | Lee |
| 2004/0066507 | A1 | 4/2004 | Kren et al. |
| 2004/0105093 | A1 | 6/2004 | Hamamatsu et al. |
| 2004/0136665 | A1 | 7/2004 | Furman et al. |
| 2004/0146295 | A1 | 7/2004 | Furman et al. |
| 2004/0252297 | A1 | 12/2004 | Fairley et al. |
| 2005/0062960 | A1* | 3/2005 | Tsuji et al. ............... 356/237.2 |

FOREIGN PATENT DOCUMENTS

| | | |
|---|---|---|
| WO | WO 00/70332 | 11/2000 |
| WO | WO 2005022969 | 3/2005 |

OTHER PUBLICATIONS

"Speckle Reduction in Pulsed-Laser Photography" by D. Kohler et al., published in Optics Communications, vol. 12, No. 1, pp. 24-28, Sep. 1974.
"Speckle Reduction with Virtual Incoherent Laser Illumination Using Modified Fiber Array", by Dingel et al., published in Optik, vol. 94, No. 3, pp. 132-136, 1993.
"Machine Vision and Applications", 1998 1:205-221, by IBM Scientists Byron E. Dom, et al.
"Programmable 2-Dimensional Microshutter Arrays", by S.H./Moseley et al, published in the ASP Conference Series, vol. XXX, 2000.
Patent Abstracts of Japan, vol. 1997, No. 03, Mar. 1997 & JP 08 292361.
Patent Abstracts of Japan, vol. 17, No. 613, Nov. 1993 & JP 05 190421.
Patent Abstracts of Japan, vol. 1996, No. 10, Oct. 1996 & JP 08 154210.
Patent Abstracts of Japan, vol. 1999, No. 04, Apr. 1999 & JP 11 014357.
Gonzales & Woods, "Digital Image Processing", Prentice-Hall, Englewood Cliffs, New Jersey, USA, 2002, pp. 273-275.
Office Action dated Apr. 27, 2009, from U.S. Appl. No. 11/764,296 (filed Jun. 18, 2007), 14 pages.
Response to Office Action filed Jul. 24, 2009, from U.S. Appl. No. 11/764,296 (filed Jun. 18, 2007), 12 pages.
Final Office Action dated Oct. 28, 2009, from U.S. Appl. No. 11/764,296 (filed Jun. 18, 2007), 15 pages.
Response to Final Office Action filed Jan. 21, 2010, from U.S. Appl. No. 11/764,296 (filed Jun. 18, 2007), 12 pages.
Office Action dated Nov. 5, 2009, from U.S. Appl. No. 12/471,752 (filed May 26, 2009), 18 pages.
Response to Office Action filed Feb. 5, 2010, from U.S. Appl. No. 12/471,752 (filed May 26, 2009), 17 pages.
Office Action dated Feb. 21, 2008, from U.S. Appl. No. 11/684,191 (filed Mar. 9, 2007), 26 pages.
Response to Office Action filed May 9, 2008, from U.S. Appl. No. 11/684,191 (filed Mar. 9, 2007), 14 pages.
Office Action dated Aug. 15, 2008, from U.S. Appl. No. 11/684,191 (filed Mar. 9, 2007), 19 pages.
Response to Office Action filed Oct. 29, 2008, from U.S. Appl. No. 11/684,191 (filed Mar. 9, 2007), 31 pages.
Final Office Action dated Jan. 26, 2009, from U.S. Appl. No. 11/684,191 (filed Mar. 9, 2007), 23 pages.
Response to Final Office Action filed Jul. 24, 2009, from U.S. Appl. No. 11/684,191 (filed Mar. 9, 2007), 7 pages.
Office Action dated Jul. 23, 3004, from U.S. Appl. No. 10/345,096 (filed Apr. 2, 2003), 15 pages.
Response to Office Action filed Nov. 24, 2004, from U.S. Appl. No. 10/345,096 (filed Apr. 2, 2003), 10 pages.
Response to European Search Report and Opinion filed May 11, 2009, from EP Patent Application No.: 07252110.7, 16pp.
European Search Report and Opinion Dated Jul. 11, 2008, from EP Patent Application No.: 07252110.7, 15pp.
European Search Report and Opinion Dated Nov. 12, 2007, from EP Patent Application No.: 07252110.7, 15pp.
European Partial Search Report and Opinion Dated Sep. 13, 2007, from EP Patent Application No.: 07252110.7, 5pp.
European Search Report Apr. 3, 2003, from EP Patent Application No.: 03250255, 5pp.
Manassah et al, Spectral Extent and Pulse Shape of the Supercontinuum for Ultrashort Laser Pulse, IEEE Journal of Quantum Electronics, vol. QE-22, No. 1, Jan. 1986, pp. 197-204.
Product Information Sheet, Koheras SuperK™ Blue, 2pp.
Hansen et al., Supercontinuum Generation in Photonic Crystal Fibers, Crystal Fibre A/S, www.crystal-fibre.com, pp. 1-11.
Office Action dated Dec. 27, 2007, from U.S. Appl. No. 11/068,711 (filed Feb. 25, 2005), 19 pages.
Response to Office Action filed Mar. 27, 2008, from U.S. Appl. No. 11/068,711 (filed Feb. 25, 2005), 8 pages.
Supplemental Response to Office Action filed May 27, 2008, from U.S. Appl. No. 11/068,711 (filed Feb. 25, 2005), 8 pages.
Final Office Action dated Sep. 30, 2008, from U.S. Appl. No. 11/068,711 (filed Feb. 25, 2005), 11 pages.
Response to Final Office Action filed Mar. 25, 2009, from U.S. Appl. No. 11/068,711 (filed Feb. 25, 2005), 5 pages.
Office Action dated Jun. 8, 2009, from U.S. Appl. No. 11/068,711 (filed Feb. 25, 2005), 11 pages.
Response to Office Action filed Sep. 8, 2009, from U.S. Appl. No. 11/068,711 (filed Feb. 25, 2005), 5 pages.
Office Action dated Sep. 29, 2009, from U.S. Appl. No. 11/068,711 (filed Feb. 25, 2005), 7 pages.
Office Action dated Sep. 29, 2009, from U.S. Appl. No. 11/410,276 (filed Apr. 24, 2006), 22 pages.
Response to Office Action filed Dec. 28, 2009, from U.S. Appl. No. 11/410,276 (filed Apr. 24, 2006), 10 pages.
Final Office Action dated Apr. 1, 2010, from U.S. Appl. No. 11/410,276 (filed Apr. 24, 2006), 21 pages.
Office Action dated Oct. 11, 2007, from U.S. Appl. No. 11/503,859 (filed Aug. 14, 2006), 9 pages.
Response to Office Action filed Jan. 11, 2008, from U.S. Appl. No. 11/503,859 (filed Aug. 14, 2006), 15 pages.
Final Office Action dated Feb. 13, 2008, from U.S. Appl. No. 11/503,859 (filed Aug. 14, 2006), 8 pages.
Response to Final Office Action filed Apr. 18, 2008, from U.S. Appl. No. 11/503,859 (filed Aug. 14, 2006), 12 pages.
Office Action dated May 1, 2008, from U.S. Appl. No. 11/503,859 (filed Aug. 14, 2006), 9 pages.
Response to Office Action filed Jul. 15, 2008, from U.S. Appl. No. 11/503,859 (filed Aug. 14, 2006), 9 pages.
Final Office Action dated Aug. 19, 2008, from U.S. Appl. No. 11/503,859 (filed Aug. 14, 2006), 12 pages.
Office Action dated Mar. 8, 2006, from U.S. Appl. No. 11/096,873 (filed Aug. 21, 2007), 13 pages.
Response to Office Action filed May 30, 2006, from U.S. Appl. No. 11/096,873 (filed Aug. 21, 2007), 15 pages.
Supplemental Response to Office Action filed Jul. 11, 2006, from U.S. Appl. No. 11/096,873 (filed Aug. 21, 2007), 7 pages.
Final Office Action dated Sep. 27, 2006, from U.S. Appl. No. 11/096,873 (filed Aug. 21, 2007), 8 pages.
Response to Final Office Action filed Oct. 20, 2006, from U.S. Appl. No. 11/096,873 (filed Aug. 21, 2007), 10 pages.
Office Action dated Oct. 20, 2005, from U.S. Appl. No. 11/021,393 (filed Dec. 23, 2004), 18 pages.
Response to Office Action filed Jan. 24, 2006, from U.S. Appl. No. 11/021,393 (filed Dec. 23, 2004), 12 pages.
Office Action dated Feb. 8, 2007, from U.S. Appl. No. 11/476,356 (filed Jun. 28, 2006), 16 pages.
Response to Office Action filed May 7, 2007, from U.S. Appl. No. 11/476,356 (filed Jun. 28, 2006), 10 pages.
Final Office Action dated Jul. 7, 2007, from U.S. Appl. No. 11/476,356 (filed Jun. 28, 2006), 5 pages.
Office Action dated Jan. 28, 2008, from U.S. Appl. No. 11/476,322 (filed Jun. 28, 2006), 18 pages.

Response to Office Action filed Apr. 23, 2008, from U.S. Appl. No. 11/476,322 (filed Jun. 28, 2006), 11 pages.
Office Action dated May 29, 2008, from U.S. Appl. No. 11/524,684 (filed Sep. 21, 2006), 26 pages.
Response to Office Action filed Aug. 25, 2008, from U.S. Appl. No. 11/524,684 (filed Sep. 21, 2006), 16 pages.
Final Office Action dated Dec. 22, 2008, from U.S. Appl. No. 11/524,684 (filed Sep. 21, 2006), 15 pages.
Response to Final Office Action filed Jun. 10, 2009, from U.S. Appl. No. 11/524,684 (filed Sep. 21, 2006), 6 pages.
Office Action dated Aug. 6, 2008, from U.S. Appl. No. 11/476,358 (filed Jun. 28, 2006), 16 pages.
Response to Office Action filed Sep. 24, 2008, from U.S. Appl. No. 11/476,358 (filed Jun. 28, 2006), 7 pages.
Office Action dated Apr. 2, 2009, from U.S. Appl. No. 11/476,358 (filed Jun. 28, 2006), 9 pages.
Response to Office Action filed Jan. 13, 2006, from U.S. Appl. No. 10/345,097 (filed Jan. 15, 2003), 6 pages.
Final Office Action dated Apr. 6, 2006, from U.S. Appl. No. 10/345,097 (filed Jan. 15, 2003), 8 pages.
Response to Final Office Action filed Jul. 6, 2006, from U.S. Appl. No. 10/345,097 (filed Jan. 15, 2003), 8 pages.
Office Action dated Sep. 7, 2006, from U.S. Appl. No. 10/345,097 (filed Jan. 15, 2003), 9 pages.
Response to Office Action filed Mar. 9, 2007, from U.S. Appl. No. 10/345,097 (filed Jan. 15, 2003), 14 pages.
Final Office Action dated May 29, 2007, from U.S. Appl. No. 10/345,097 (filed Jan. 15, 2003), 9 pages.
Response to Final Office Action filed Oct. 1, 2007, from U.S. Appl. No. 10/345,097 (filed Jan. 15, 2003), 10 pages.
Response to Final Office Action filed Nov. 29, 2007, from U.S. Appl. No. 10/345,097 (filed Jan. 15, 2003), 6 pages.
Office Action dated Mar. 4, 2008, from U.S. Appl. No. 10/345,097 (filed Jan. 15, 2003), 10 pages.
Response to Office Action filed Aug. 25, 2008, from U.S. Appl. No. 10/345,097 (filed Jan. 15, 2003), 9 pages.
Watkins, L.S., Inspection of Integrated Circuit Photomasks with Intensity Spatial Filters, Proceedings of the IEEE, vol. 37, No. 9, Sep. 1969, pp. 1634-1639.
Axelrod, N. N. et al., Intensity Spatial Filtering Applied to Defect Detection in Integrated Photomasks, Proceedings of the IEEE, Apr. 1972, pp. 447-448.
Ghosh et al., Real-Time Defect Inspection of Periodic Patterns Using Self-Pumped Barium Titanate Crystal, Optics Communications, vol. 77, No. 2, 3, Jun. 15, 1990, pp. 135-138.
Negevtech, Ltd.: PCT/IL04/00022 filed Jan. 11, 2004, International Search Report as published dated Nov. 8, 2004, ISA/US, 4pp.
Negevtech, Ltd.; PCT/IL04/00022 filed Jan. 11, 2004, Written Opinion dated Nov. 8, 2004. ISA/US, 4pp.
Negevtech, Ltd.; PCT/IL04/00023 filed Jan. 11, 2004, International Search Report and Written Opinion dated Sep. 12, 2007. ISA/US, 8pp.

* cited by examiner

FIG. 1B

FROM STEP 50 IN FIG. 1A

60 — FOR EACH SMALL CURRENT IMAGE, SELECT AT LEAST ONE PREDETERMINED SET OF (E.G. 4 – 40) MAXIMAL MAXIMUM DIFFERENCE PIXELS COMPRISING SMALL CURRENT IMAGE PIXELS WHICH ARE MAXIMAL. OUTPUT=SETS (ONE SET PER SMALL CURRENT IMAGE, IF MAXIMAL MAXIMUM DIFFERENCE PIXELS ARE DETERMINED GLOBALLY, AND SEVERAL SETS PER SMALL CURRENT IMAGE, IF MAXIMAL MAXIMUM DIFFERENCE PIXELS ARE DETERMINED LOCALLY) OF LOCATIONS OF POSSIBLE DEFECTS ("ALARMS").

70 — THRESHOLD THE ALARMS SO AS TO FILTER OUT INDIVIDUAL ALARMS WHOSE VALUES IN THE DIFFERENCE IMAGE ARE LOW RELATIVE TO THE VALUES OF THE NON-ALARM PIXELS IN THAT SLICE OF THE DIFFERENCE IMAGE WHOSE GRAY LEVELS, IN THE REFERENCE IMAGE, ARE SIMILAR TO THE GRAY LEVELS, IN THE REFERENCE IMAGE, OF THE INDIVIDUAL ALARM AND SO AS TO RETAIN INDIVIDUAL ALARMS WHOSE VALUES IN THE DIFFERENCE IMAGE ARE HIGH

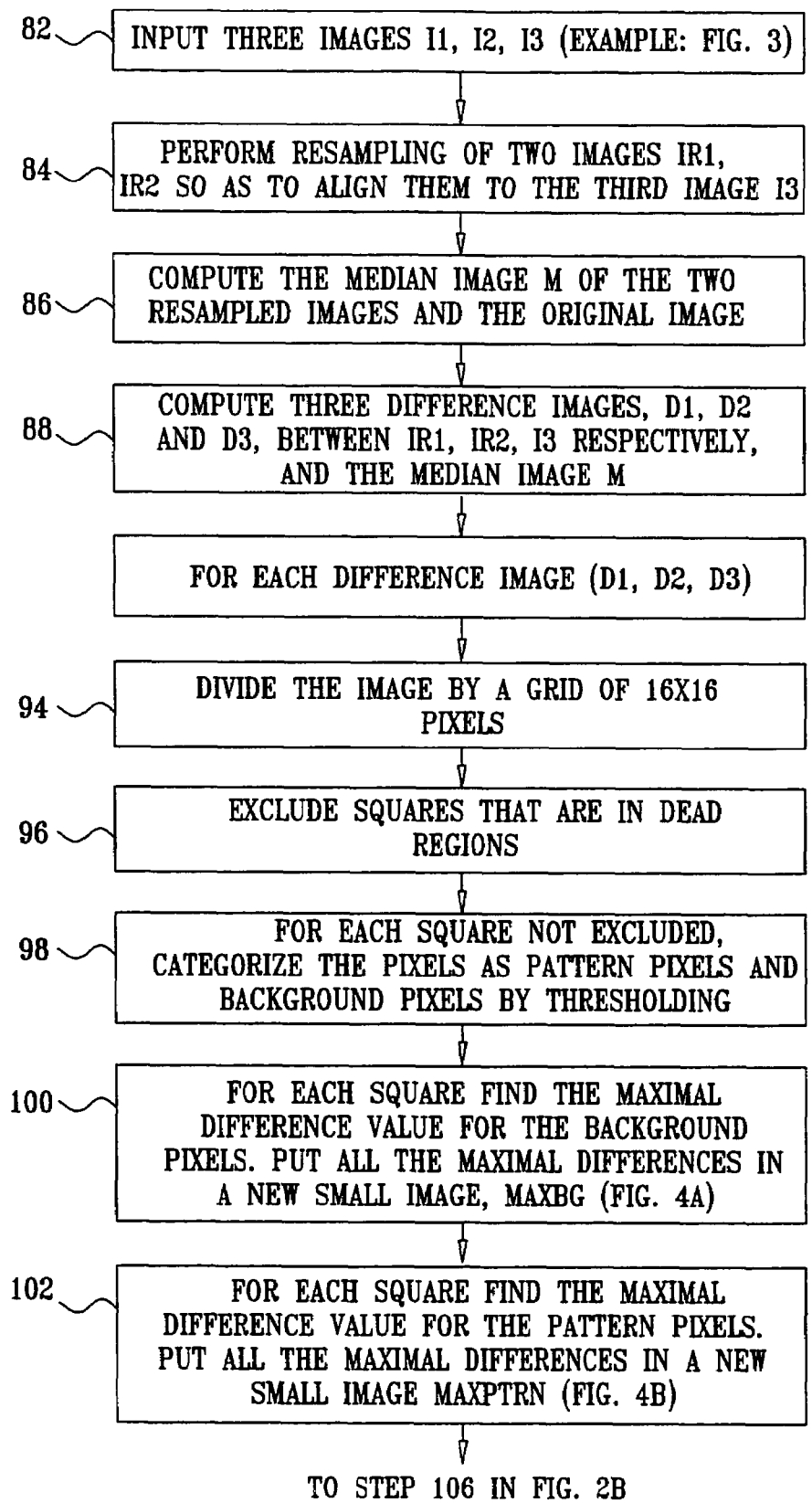

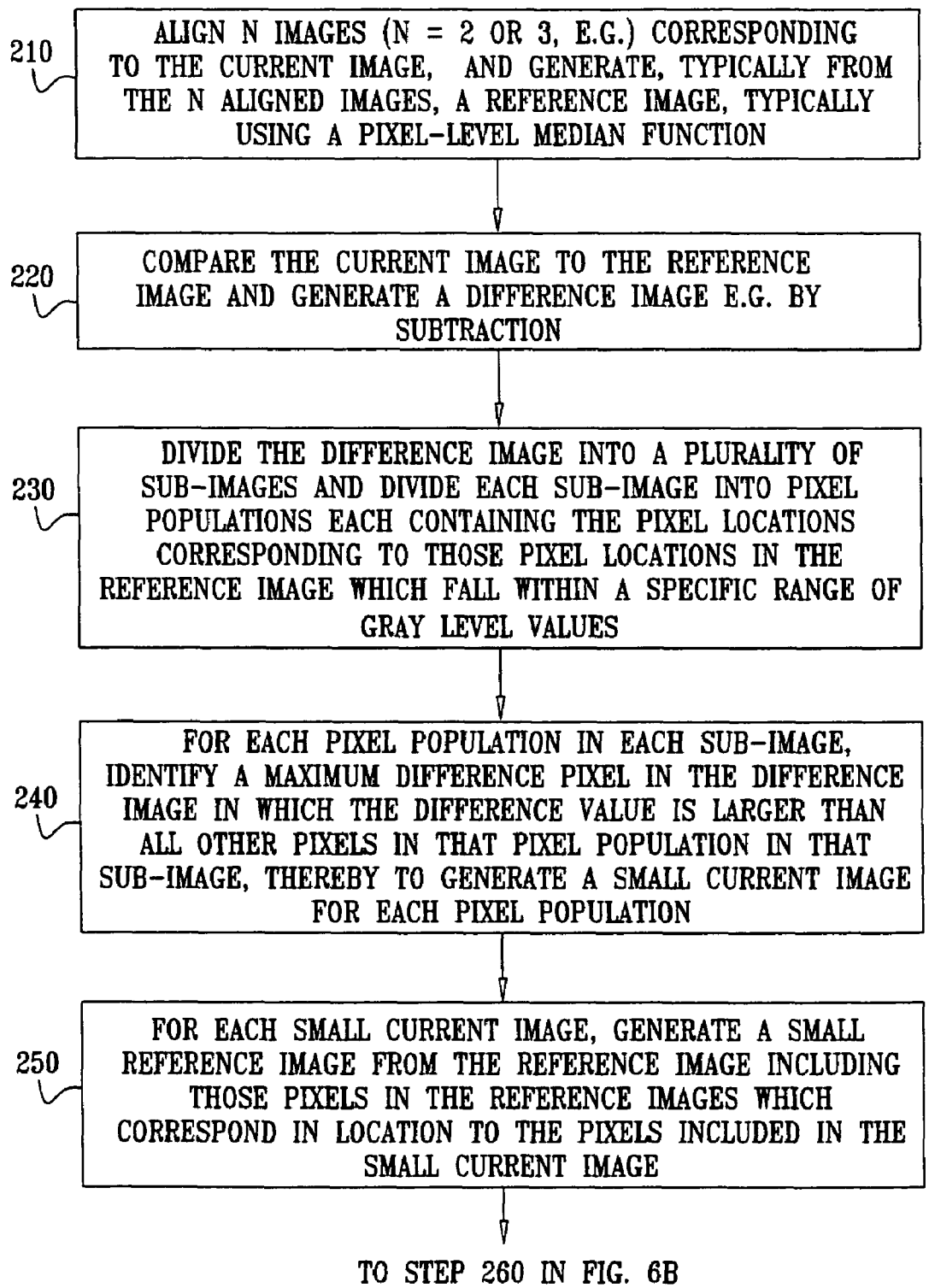

FIG. 8B    FROM STEP 440 IN FIG.8A

460 — FOR EACH SMALL CURRENT IMAGE, SELECT AT LEAST ONE PREDETERMINED SET OF (E.G. 4 - 40) MAXIMAL MAXIMUM BRIGHTNESS PIXELS COMPRISING SMALL CURRENT IMAGE PIXELS WHICH ARE LOCALLY (IN WHICH CASE SEVERAL SETS ARE DEFINED) OR GLOBALLY (IN WHICH CASE A SINGLE SET IS DEFINED) MAXIMAL, WHERE LOCAL MAXIMALITY IS DETERMINED FOR EACH SLICE OF GRAY LEVELS (GRAY LEVEL BIN) WITHIN THE SMALL REFERENCE IMAGE. THE OUTPUT OF THIS STEP IS SETS (ONE SET PER SMALL CURRENT IMAGE, IF MAXIMAL MAXIMUM BRIGHTNESS PIXELS ARE DETERMINED GLOBALLY, AND SEVERAL SETS PER SMALL CURRENT IMAGE, IF MAXIMAL MAXIMUM BRIGHTNESS PIXELS ARE DETERMINED LOCALLY) OF LOCATIONS OF POSSIBLE DEFECT PIXELS ("ALARM PIXELS")

470 — OPTIONALLY, TO REDUCE COMPUTING POWER REQUIREMENTS, THRESHOLD THE ALARM PIXELS SO AS TO FILTER OUT INDIVIDUAL ALARM PIXELS WHOSE VALUES IN THE CURRENT ALIGNED IMAGE ARE LOW RELATIVE TO THE VALUES OF THE NON-ALARM PIXELS AND SO AS TO RETAIN "STRONG" INDIVIDUAL ALARM PIXELS WHOSE VALUES IN THE CURRENT ALIGNED IMAGE ARE HIGH RELATIVE TO THE VALUES OF THE NON-ALARM PIXELS

510 — COMPUTE A THRESHOLD BRIGHTNESS LEVEL-E.G. THE 90TH PERCENTILE BRIGHTNESS LEVEL-FOR PIXELS WITHIN THAT ALIGNED IMAGE

520 — COMPUTE, FOR EACH "STRONG" ALARM PIXEL, A "VICINITY STRENGTH PARAMETER", TYPICALLY COMPRISING THE SUM OF THE BRIGHTNESSES OF ALL OF ITS VICINITY PIXELS (E.G. THE 5 X 5 PIXELS SURROUNDING IT), NORMALIZED TO TAKE INTO ACCOUNT THE GENERAL NOISE LEVEL OF THE CURRENT ALIGNED IMAGE

530 — DEFINE A THRESHOLD VICINITY STRENGTH AND DEFINE ALL "STRONG" ALARM PIXEL VICINITIES WHOSE VICINITY STRENGTH EXCEEDS THAT THRESHOLD, AS DEFECTS

TO STEP 650 IN FIG. 10B

FIG. 10B

FROM STEP 640 IN FIG. 10A

650 — GENERATE A SMALL IMAGE FOR EACH BIN, INCLUDING ONLY THOSE MAXIMAL DIFFERENCE VALUES I.E. CONTAINING ONLY ONE PIXEL PER SUB-IMAGE. IF A BIN IS NOT REPRESENTED IN A PARTICULAR SUB-IMAGE, THE PIXEL CORRESPONDING TO THAT SUB-IMAGE IN THAT BIN'S SMALL IMAGE IS TYPICALLY GIVEN A VALUE OF 0

660 — FOR EACH SMALL IMAGE, SELECT AT LEAST ONE PREDETERMINED SET OF (E.G. 4 - 40) MAXIMAL MAXIMUM DIFFERENCE PIXELS COMPRISING SMALL IMAGE PIXELS WHICH ARE LOCALLY MAXIMAL (IN WHICH CASE SEVERAL SETS ARE DEFINED) OR GLOBALLY MAXIMAL (IN WHICH CASE A SINGLE SET IS DEFINED) WHERE LOCAL MAXIMALITY IS DETERMINED FOR EACH SLICE OF GRAY LEVELS (GRAY LEVEL BIN) WITHIN THE SMALL REFERENCE IMAGE. THE OUTPUT OF THIS STEP IS SETS (ONE SET PER SMALL CURRENT IMAGE, IF MAXIMAL MAXIMUM DIFFERENCE PIXELS ARE DETERMINED GLOBALLY AND SEVERAL SETS PER SMALL CURRENT IMAGE, IF MAXIMAL MAXIMUM DIFFERENCE PIXELS ARE DETERMINED LOCALLY) OF LOCATIONS OF POSSIBLE DEFECT PIXELS ("ALARM PIXELS")

670 — OPTIONALLY, TO REDUCE COMPUTING POWER REQUIREMENTS, THRESHOLD THE ALARM PIXELS SO AS TO FILTER OUT INDIVIDUAL ALARM PIXELS WHOSE VALUES IN THE DIFFERENCE IMAGE ARE LOW RELATIVE TO THE VALUES OF THE NON-ALARM PIXELS IN THAT SLICE OF THE DIFFERENCE IMAGE WHOSE GRAY LEVELS, IN THE ORIGINAL IMAGE, ARE SIMILAR TO THE GRAY LEVELS, IN THE ORIGINAL IMAGE, OF THE INDIVIDUAL ALARM PIXEL AND SO AS TO RETAIN "STRONG" INDIVIDUAL ALARM PIXELS WHOSE VALUES IN THE DIFFERENCE IMAGE ARE HIGH RELATIVE TO THE VALUES OF THE NON-ALARM PIXELS IN THAT SLICE OF THE DIFFERENCE IMAGE WHOSE GRAY LEVELS, IN THE ORIGINAL IMAGE, ARE SIMILAR TO THE GRAY LEVELS, IN THE ORIGINAL IMAGE, OF THE INDIVIDUAL ALARM

FIG. 14A

810 — GENERATE AT LEAST 3 INPUT IMAGES, INCLUDING AN ORIGINAL, FIRST INPUT IMAGE OF A REPETITIVELY PATTERNED OBJECT AND AT LEAST TWO ADDITIONAL IMAGES OF THE REPETITIVELY PATTERNED OBJECT, EACH TRANSLATED ONE OR A FEW CELLS AWAY FROM THE ORIGINAL INPUT IMAGE IN A PARTICULAR DIRECTION. USE THE SAME-SMEAR FILTER OF FIG. 13 ON EACH OF THE AT LEAST THREE IMAGES INCLUDING THE ORIGINAL IMAGE, THEREBY TO GENERATE AT LEAST THREE SAME-SMEAR ALIGNED IMAGES

820 — COMPARE EACH OF THE N SAME-SMEAR ALIGNED IMAGES TO THE REFERENCE IMAGE AND GENERATE, FOR EACH, A DIFFERENCE IMAGE E.G. BY SUBTRACTION. THE K'TH DIFFERENCE IMAGE (K = 1, ...N) IS THEN THE DIFFERENCE IMAGE REPRESENTING DIFFERENCES BETWEEN THE REFERENCE AND THE K'TH SAME-SMEAR ALIGNED IMAGE

830 — COMPUTE THE DIFFERENCES BETWEEN CORRESPONDING PIXELS IN EACH PAIR OF SAME-SMEAR ALIGNED IMAGES. THE K'TH PAIR OF SAME-SMEAR ALIGNED IMAGES IS A PAIR WHICH DOES NOT INCLUDE THE K'TH ALIGNED IMAGE. FOR EACH PAIR OF SAME-SMEAR ALIGNED IMAGES, DEFINE "BINS" EACH COMPRISING A SUB-RANGE OF VALUES WITHIN THE TOTAL RANGE OF VALUES FOUND. FOR EXAMPLE, IF THE DIFFERENCES BETWEEN THE CORRESPONDING PIXELS IN ALIGNED IMAGES 2 AND 3 ARE FOUND TO VARY BETWEEN 0 AND 100 GRAY LEVELS, THE FOLLOWING 5 BINS MAY BE DEFINED: 0 - 20, 20 - 40, 40 - 60, 60 - 80 AND 80 - 100 GRAY LEVELS. CATEGORIZE THE PIXELS OF THE K'TH DIFFERENCE IMAGE GENERATED IN STEP 820, USING THE BINS IDENTIFIED FOR THE K'TH PAIR OF SAME-SMEAR ALIGNED IMAGES

TO STEP 840 IN FIG. 14B

FIG. 14B  FROM STEP 830 IN FIG. 14A

840 — DIVIDE EACH DIFFERENCE IMAGE INTO A PLURALITY OF SUB-IMAGES E.G. 16 X 16 SUB-IMAGES. FOR EACH BIN (AS DEFINED IN STEP 830) IN EACH SUB-IMAGE, FIND THE PIXEL HAVING THE MAXIMAL DIFFERENCE VALUE. GENERATE A SMALL IMAGE FOR EACH BIN, INCLUDING ONLY THOSE MAXIMAL DIFFERENCE VALUES I.E. CONTAINING ONLY ONE PIXEL PER SUB-IMAGE. IF A BIN IS NOT REPRESENTED IN A PARTICULAR SUB-IMAGE, THE PIXEL CORRESPONDING TO THAT SUB-IMAGE IN THAT BIN'S SMALL IMAGE IS TYPICALLY GIVEN A VALUE OF 0

860 — FOR EACH SMALL IMAGE, SELECT AT LEAST ONE PREDETERMINED SET OF (E.G. 4 - 40) MAXIMAL MAXIMUM DIFFERENCE PIXELS COMPRISING SMALL IMAGE PIXELS WHICH ARE LOCALLY MAXIMAL (IN WHICH CASE SEVERAL SETS ARE DEFINED) OR GLOBALLY MAXIMAL (IN WHICH CASE A SINGLE SET IS DEFINED) WHERE LOCAL MAXIMALITY IS DETERMINED FOR EACH SLICE OF GRAY LEVELS (GRAY LEVEL BIN) WITHIN THE SMALL REFERENCE IMAGE. THE OUTPUT OF THIS STEP IS SETS (ONE SET PER SMALL CURRENT IMAGE, IF MAXIMAL MAXIMUM DIFFERENCE PIXELS ARE DETERMINED GLOBALLY AND SEVERAL SETS PER SMALL CURRENT IMAGE, IF MAXIMAL MAXIMUM DIFFERENCE PIXELS ARE DETERMINED LOCALLY) OF LOCATIONS OF POSSIBLE DEFECT PIXELS ("ALARM PIXELS")

870 — OPTIONALLY, TO REDUCE COMPUTING POWER REQUIREMENTS, THRESHOLD THE ALARM PIXELS SO AS TO FILTER OUT INDIVIDUAL ALARM PIXELS WHOSE VALUES IN THE DIFFERENCE IMAGE ARE LOW RELATIVE TO THE VALUES OF THE NON-ALARM PIXELS IN THAT SLICE OF THE DIFFERENCE IMAGE WHOSE GRAY LEVELS, IN THE ORIGINAL IMAGE, ARE SIMILAR TO THE GRAY LEVELS, IN THE ORIGINAL IMAGE, OF THE INDIVIDUAL ALARM PIXEL AND SO AS TO RETAIN "STRONG" INDIVIDUAL ALARM PIXELS WHOSE VALUES IN THE DIFFERENCE IMAGE ARE HIGH RELATIVE TO THE VALUES OF THE NON-ALARM PIXELS IN THAT SLICE OF THE DIFFERENCE IMAGE WHOSE GRAY LEVELS, IN THE ORIGINAL IMAGE, ARE SIMILAR TO THE GRAY LEVELS, IN THE ORIGINAL IMAGE, OF THE INDIVIDUAL ALARM

METHOD AND APPARATUS FOR DETECTING DEFECTS IN WAFERS

FIELD OF THE INVENTION

The present invention relates to image processing generally, and more particularly to inspection of microscopic objects such as wafers.

BACKGROUND OF THE INVENTION

The following prior art documents are believed to summarize the state of the art:

U.S. Pat. Nos. 5.982.921; 4,579,455; 4,969,198; 4,805,123; 5,185,812; 6,818,459; 6,816.249; 6.282.309; 6.081.325; 6,078,386; 6,020,957; 5.917,588; 5,825,482; 4,845,558; 4.579,455; and 4.532.650, and published U.S. Patent Application US20040066507A1.

SUMMARY OF THE INVENTION

The present invention seeks to provide an improved system and method for inspection of microscopic objects such as wafers. There is thus provided in accordance with a preferred embodiment of the present invention, a method for inspecting a wafer including a multiplicity of dies the method comprising dividing an image of at least a portion of the wafer into a plurality of sub-images each representing a sub-portion of the wafer, and selecting at least one defect candidate within each sub-image by comparing each sub-image to a corresponding sub-image of a reference comprising a representation, which is assumed to be defectless, of the portion of the wafer.

It is appreciated that the above method may employ any periodic unit of comparison, such as but not limited to one or more fields, dies or cells, to detect defects by comparing a potentially defective portion of a wafer to be inspected to a reference based on an identical portion of the wafer which typically comprises a periodic repetition of the portion to be inspected.

Further in accordance with a preferred embodiment of the present invention the method includes generating the reference by providing and aligning a plurality of images of the wafer and computing a median of the pixel values of the plurality of aligned images at each pixel location.

Still further in accordance with a preferred embodiment of the present invention, the method includes performing further defect detection analysis on a subset of the defect candidates, the subset comprising a predetermined number of best defect candidates.

Yet further in accordance with a preferred embodiment of the present invention, the further defect detection analysis includes identifying defect candidates which differ from their respectively corresponding locations in the reference image by more than a threshold value, the threshold value used for an individual defect candidate located at an individual location within the first image being a function of estimated variance between different images of the individual location.

Additionally in accordance with a preferred embodiment of the present invention, the method includes estimating variance between different images of the individual location by estimating variance, at each of a multiplicity of locations, between at least two different images of each such location.

Further in accordance with a preferred embodiment of the present invention, the step of estimating variance also includes estimating variance, at each of a multiplicity of similar locations, between at least two different images of each such location.

Additionally in accordance with a preferred embodiment of the present invention, the identical sub-portion includes at least a portion of a die that is identical to a die, within the sub-image, which is being inspected.

Also in accordance with a preferred embodiment of the present invention, the method includes dividing at least one of the sub-images into portions which it is desired to inspect separately; and, for each portion, performing further defect detection analysis on a subset of the defect candidates belonging to the portion, the subset including a predetermined number of those defect candidates within the portion which have the highest difference values.

Yet further in accordance with a preferred embodiment of the present invention, the image includes patternless i.e. bare portions, and the step of selecting at least one defect candidate within each sub-image includes selecting the pixel within each sub-image with the largest gray level value.

Also in accordance with a preferred embodiment of the present invention, the image also includes bright portions reflecting a large amount of light, and defect candidates are not selected within the bright portions.

Further in accordance with a preferred embodiment of the present invention, the dividing step includes dividing at least one of the sub-images into portions each having a defined gray level range in the reference.

Yet further in accordance with a preferred embodiment of the present invention, the dividing step includes dividing at least one of the sub-images into portions each having a defined gray level range in a gradient of the reference.

Conventional methods for computing a gradient of an image are described in Jain, Anil K., *Fundamentals of Digital Image Processing*, Prentice-Hall, Englewood Cliffs, N.J., USA, 1989, (henceforth "Jain"), pages 347-350.

Still further in accordance with a preferred embodiment of the present invention, the dividing step includes dividing at least one of the sub-images into portions, the portions having a defined gray level range in a difference image generated from a plurality of images of the portion of the wafer.

Additionally in accordance with a preferred embodiment of the present invention, the difference image is generated by comparing an image of the portion of the wafer to another image of the same portion.

Still further in accordance with a preferred embodiment of the present invention, the selecting step includes generating, for each sub-image, a difference sub-image representing the difference between the sub-image and a reference representing at least one identical sub-portion of the wafer and selecting at least one maximal difference value within the difference sub-image as a defect candidate.

Yet further in accordance with a preferred embodiment of the present invention, the method includes performing further defect detection analysis on a subset of the defect candidates, the subset including a predetermined number of those defect candidates having the highest difference values.

Still further in accordance with a preferred embodiment of the present invention, the wafer portion includes a multiplicity of cells each including a repeating portion of a pattern on the wafer, and the identical sub-portion includes at least a portion of a cell which is identical to a cell, within the sub-image, which is being inspected.

Also provided, in accordance with another preferred embodiment of the present invention, is a method for inspecting a wafer including a multiplicity of dies, the method including comparing a first image of at least a portion of the wafer to a reference image and identifying locations in the first image which differ from the reference image by more than a threshold value, the threshold value used for an individual location within the first image being a function of estimated variance between different images of the individual location.

Further in accordance with a preferred embodiment of the present invention, the method includes estimating variance between different images of the individual location by estimating variance, at each of a multiplicity of locations, between at least two different images of each such location.

Still further in accordance with a preferred embodiment of the present invention, the step of estimating variance includes estimating variance at each of a multiplicity of similar locations, between at least two different images of each such location.

Further provided, in accordance with still another preferred embodiment of the present invention, is a method for inspecting at least a portion of a wafer including a multiplicity of dies, the method including inspecting a multiplicity of locations within an image of at least a portion of the wafer to be inspected and selecting a plurality of defect candidates, scoring the plurality of defect candidates, and selecting a predetermined number of the highest scoring defect candidates for further defect detection analysis.

Additionally in accordance with a preferred embodiment of the present invention, the inspecting step includes comparing the multiplicity of locations within at least a portion of the wafer to be inspected with a multiplicity of references, and quantifying the differences therebetween, thereby to obtain a corresponding multiplicity of difference values characterizing the multiplicity of locations respectively.

Still further in accordance with a preferred embodiment of the present invention, the significant criterion includes the signal to noise ratio of the image.

Yet further provided, in accordance with still another preferred embodiment of the present invention, is a method for inspecting a wafer including a multiplicity of dies, the method including, for each of a multiplicity of locations of the wafer, sorting discrepancies found between individual ones of a plurality of representations of the wafer location into larger and smaller discrepancies, and determining whether or not each location is a defect, based on the magnitude of at least one larger discrepancy for that location relative to the magnitude of at least one smaller discrepancy for that location.

Additionally provided, in accordance with yet another preferred embodiment of the present invention, is a method for inspecting a defective image of a wafer including a multiplicity of dies, the method including generating a difference image comprising differences between a multiplicity of locations within the defective image and a corresponding multiplicity of locations within a reference, the difference image defining a distribution of difference values; and selecting, as defects, individual ones from among the multiplicity of locations whose difference values are characterized as defects based on a defect definition function which is a predetermined function of the distribution of difference values.

Further in accordance with a preferred embodiment of the present invention, the multiplicity of locations within the reference is divided into a plurality of bins each having defined characteristics, each bin defining a distribution of difference values at the locations in the difference image corresponding to the locations within that bin, and the selecting step includes selecting, as a defect, at least one individual location from among the multiplicity of locations whose difference value answers to a defect definition function which is a predetermined function of the distribution of difference values within the bin to which the individual location belongs.

Still further in accordance with a preferred embodiment of the present invention, the selecting step includes selecting, as a defect, at least one individual set of adjacent locations whose difference values answer to a defect definition function which is a combination of predetermined functions of the distributions of difference values within the bins to which the adjacent locations respectively belong.

Yet further in accordance with a preferred embodiment of the present invention, the set of adjacent locations comprises a matrix of adjacent pixels.

Additionally in accordance with a preferred embodiment of the present invention, each predetermined function of the distribution of difference values within a bin to which an adjacent location belongs includes a function of an average of all difference values in the bin to which the adjacent location belongs which exceed a predetermined high percentile difference value within that bin.

Still further in accordance with a preferred embodiment of the present invention, each predetermined function includes a normalized function having a normalization factor based on the noise level within the bin to which the adjacent location, associated with the predetermined function, belongs.

Yet further in accordance with a preferred embodiment of the present invention, the predetermined function includes a multiple of a high percentile difference value.

Also in accordance with a preferred embodiment of the present invention, the predetermined function includes a multiple of a combination of a subset of high-value difference values.

Additionally in accordance with a preferred embodiment of the present invention, the predetermined function includes a multiple of an average of all difference values in the difference image which exceed a predetermined high percentile difference value.

Additionally provided, in accordance with another preferred embodiment of the present invention, is a method for inspecting a wafer including a multiplicity of dies, the method comprising providing at least three images of identical portions of the microscopic image, including adding smear to at least one of the images so as to generate an identical amount of smear in the at least three images, combining the at least three images having identical amounts of smear into a reference, and inspecting each of a plurality of images of a corresponding plurality of portions of a wafer to be inspected relative to the reference.

Further provided, in accordance with a preferred embodiment of the present invention, the providing step includes aligning the at least three identical portions of the microscopic image, thereby to provide at least three mutually aligned images.

Also in accordance with a preferred embodiment of the present invention, the aligning includes selecting a re-sampling kernel to apply to each of the identical portions characterized in that the identical portions, once re-sampled using the kernels, have an identical amount of smear.

Also provided, in accordance with a preferred embodiment of the present invention, the aligning includes, if a sub-portion's misalignment (dx,dy) relative to a selected alignment marker is 0.5 pixel, using a (0.5,0.5) filter, and otherwise, using a re-sampling filter of order n>2, that generates a shifted image with shift (dx,dy) by convolution with the original image, and whose frequency response approximates the frequency response of the (0.5,0.5) filter. A filter of order n is a filter whose coefficients are polynomials of order n.

A particular feature of the alignment process shown and described herein is that the smear is independent of the sub-pixel component of the alignment process. Therefore, if the sub-pixel component used to align the first identical sub-portion differs from the sub-pixel component used to align the second and/or third identical sub-portions, the smear in the aligned first identical sub-portion will nonetheless be the same as the smear in the aligned second and third identical sub-portions.

Additionally provided, in accordance with yet another preferred embodiment of the present invention, is apparatus for inspecting a wafer including a multiplicity of dies, including an image divider, operative to divide an image of at least a portion of the wafer into a plurality of sub-images each representing a sub-portion of the wafer; and a defect candidate identifier, operative to identify at least one defect candidate within each sub-image, by comparing each sub-image to a corresponding sub-image of a reference comprising a representation, which is assumed to be defectless, of the portion of the wafer.

Yet further provided, in accordance with another preferred embodiment of the present invention, is apparatus for inspecting a wafer including a multiplicity of dies, including an image comparator, operative to compare a first image of at least a portion of the wafer to a reference image and to identify locations in the first image which differ from the reference image by more than a threshold value, the threshold value used for an individual location within the first image being a function of estimated noise between different images of the individual location.

Still further provided, in accordance with another preferred embodiment of the present invention, is apparatus for inspecting at least a portion of a wafer including a multiplicity of dies, including a defect candidate identifier, operative to inspect a multiplicity of locations within an image of a wafer to be inspected and to select a plurality of defect candidates, and a defect candidate analyzer, operative to score the plurality of defect candidates and to select a predetermined number of the highest scoring defect candidates for further defect detection analysis.

Also provided, in accordance with still another preferred embodiment of the present invention, is apparatus for inspecting a wafer including a multiplicity of dies including a discrepancy sorter operative, for each of a multiplicity of locations of the wafer, to sort discrepancies found between individual ones of a plurality of representations of the wafer location into larger and smaller discrepancies, and a discrepancy analyzer, operative to determine whether or not each location is a defect, based on the magnitude of the larger discrepancy for that location relative to the magnitude of the smaller discrepancy for that location.

Yet further provided, in accordance with another preferred embodiment of the present invention, is apparatus for inspecting a defective image of a wafer including a multiplicity of dies, including a difference image generator operative to generate a difference image comprising differences between a multiplicity of locations within the defective image and a corresponding multiplicity of locations within a reference, the difference image defining a distribution of difference values, and a defect identifier operative to select, as defects, individual ones from among the multiplicity of locations whose difference values answer to a defect definition function which is a predetermined function of the distribution of difference values.

Further provided, in accordance with another preferred embodiment of the present invention, is apparatus for inspecting a wafer including a multiplicity of dies, including an image generator operative to provide at least three images of identical portions of the microscopic object and to add smear to at least one of the images so as to generate an identical amount of smear in the at least three images, a reference image generator operative to combine the at least three images having identical amounts of smear into a reference, and an image inspector operative to inspect each of a plurality of images of a corresponding plurality of portions of a wafer to be inspected, relative to the reference.

According to a preferred embodiment of the present invention, image noise is taken into account through the peer-group based filtering concept. An alarm's strength is defined by the defect's peak difference divided by the mean of the upper 10% (say) in the relevant bin. In order to pass to the next stage an alarm's strength must be higher than a defined threshold which may be given in a configurational file in the system.

It is appreciated that defect sensitivity may be set by the user, using a defect sensitivity slider which the user manipulates. Any suitable measure may define defect sensitivity for the purposes of the defect sensitivity slider, such as a peer-group based measure as described above. Alternatively, particularly when inspecting dark-field illuminated images and particularly when working in "bare mode". as described herein, the measure represented by the defect sensitivity slider may be based on the signal to noise ratio (SNR) of the alarm, which is a known criterion for estimating the significance of an alarm. The signal is the differences (with noise weighting). divided by a measurement of the noise. If the signal to noise ratio is used, the sensitivity slider typically permits the operator to determine a threshold signal to noise ratio, such that a pixel is considered a defect if and only if its signal to noise ratio value exceeds the threshold.

Typically, cell-to-cell inspection methods accept as input an original image with repeating cells and two other images shifted by an integer number of cells (typically one) from the original. A same-smear method such as that shown and described herein may be employed to re-sample the two shifted images and generate equal smear between the shifted images and the original image.

In contrast to the method shown and described herein as particularly suitable for dark-field illuminated objects in which gray level (GL) is used to separate background pixels from pattern pixels, in bright field applications, the filtered difference of 2 images may be computed, to separate color-varied and non-color-variated pixels in the third image. After categorizing the pixels of the reference image into bins and computing difference images, the method divides the difference images to 16×16 pixel squares and computes the maximal difference on the color-variated and non-color-variated pixels. From these maximal differences it generates two much smaller images that contain the maximal difference values for each square for the color-variated and for the non-color-variated pixels. Based on these images the method finds the squares with maximal difference for each bin and filters them by their difference strength, relative to the differences characteristic of peers.

In order to compare images all images are typically mutually aligned. Aligning of images involves the determination of the relative geometric translation ("registration"). followed by re-sampling of all or part of the images towards a mutual point ("re-sampling"). In order to achieve accurate alignment sub-pixel re-sampling should be employed. The new image pixels are computed by using conventional interpolation methods such as but not limited to Nearest neighbor methods and Bilinear interpolation bi-cubic interpolation methods as described in the above-referenced Jain textbook pages 253-255. Many interpolation methods cause image "smearing" although the Nearest Neighbor method typically does not. The closer the displacement is to half a pixel the larger the smearing is. More information regarding interpolation methods can be found in Gonzales & Woods. *Digital Image Processing*, Prentice-Hall, Englewood Cliffs, N.J. USA. 2002. pages 273-275.

According to one alternative embodiment of the present invention, bilinear re-sampling is applied to three. e.g. images of a portion of an object, "toward" a fourth image of that portion. As a result the three re-sampled images are visibly more "smeared" than the image toward which they were re-sampled, causing high artificial differences near the edges. Those differences are translated to misdetection as well as false alarms depending on the threshold strategy. To reduce these artifacts, one or more of the following 3 solutions may be employed:

a. More accurate re-sampling methods, such as 4×4 bicubic re-sampling.

b. Optimization of the re-sampling point: For comparison between 2 images, with relative displacement $d_{ab}$, the optimal re-sampling would be splitting the non-integer portion of $d_{ab}$ equally between the two images. This way, the "smearing" in the 2 images would be both similar and minimal. For higher orders, the benefit that may be gained grows smaller. It may be shown that the benefit behaves as $f(n)=(\frac{1}{2}-\frac{1}{2}n)$, where n is the number of images being aligned, which is the minimal maximum sub-pixel shift that can be used. For n=2, the images can be aligned to a middle point, the shift being of identical magnitude for the two images, but in opposite directions. The maximal shift in this case is ¼. However, for n>2, shifts of the images are different, the maximal shift is f(n) and the smearing is not identical when all images are shifted, but closer than the possibility of shifting only some of them.

c. Equal smearing of all images: A new interpolation filter that has been composed of two complementing components performs "Equal smearing". The two components are: re-sampling filter and smear filter. The smearing component compensates for the re-sampling component so that as a whole, the filter has a constant smearing effect. For example, when dX=dY=0. the smearing component is maximal, so that the effect would resemble the smearing caused by a half a pixel translation.

According to a preferred embodiment of the present invention defect pixels may be identified using n images of an object portion to be inspected by comparing difference images generated from the n images to one another to identify deviant pixels in the difference images.

Generally, any pixel-by-pixel subtraction-based comparison mentioned herein may be replaced by any other suitable comparison metric such as subtraction of a function of each pixel value in one image from the same or a different function of each corresponding pixel value in another image.

BRIEF DESCRIPTION OF THE DRAWINGS

The present invention will be understood and appreciated from the following detailed description, taken in conjunction with the drawings in which:

FIGS. 1A-1B, taken together, form a simplified flowchart illustration of a die-to-die, peer-group filter based method for inspecting dark-field illuminated images of a microscopic object in accordance with a preferred embodiment of the present invention;

FIGS. 2A, 2B, and 2C, taken together, form a simplified flowchart illustration of a preferred implementation of the method of FIGS. 1A-1B;

FIGS. 6A-6B, taken together, form a simplified flowchart illustration of a die-to-die, SNR filter based method for inspecting dark-field illuminated images in accordance with a preferred embodiment of the present invention;

FIGS. 8A-8B, taken together, form a simplified flowchart illustration of a preferred method of inspecting images particularly useful when it is known in advance that a wafer image is, other than defects, substantially blank or bare;

FIGS. 10A-10B, taken together, form a simplified flowchart illustration of an image inspection method operative in accordance with a preferred embodiment of the present invention, which is particularly suitable for performing die-to-die inspection of images of bright-field illuminated objects;

FIGS. 14A-14B, taken together, form a simplified flowchart illustration of an image inspection method operative in accordance with a preferred embodiment of the present invention, which is particularly suitable for performing cell-to-cell inspection of images of bright-field illuminated (or dark-field illuminated) objects;

DETAILED DESCRIPTION OF A PREFERRED EMBODIMENT

Figure 1A:
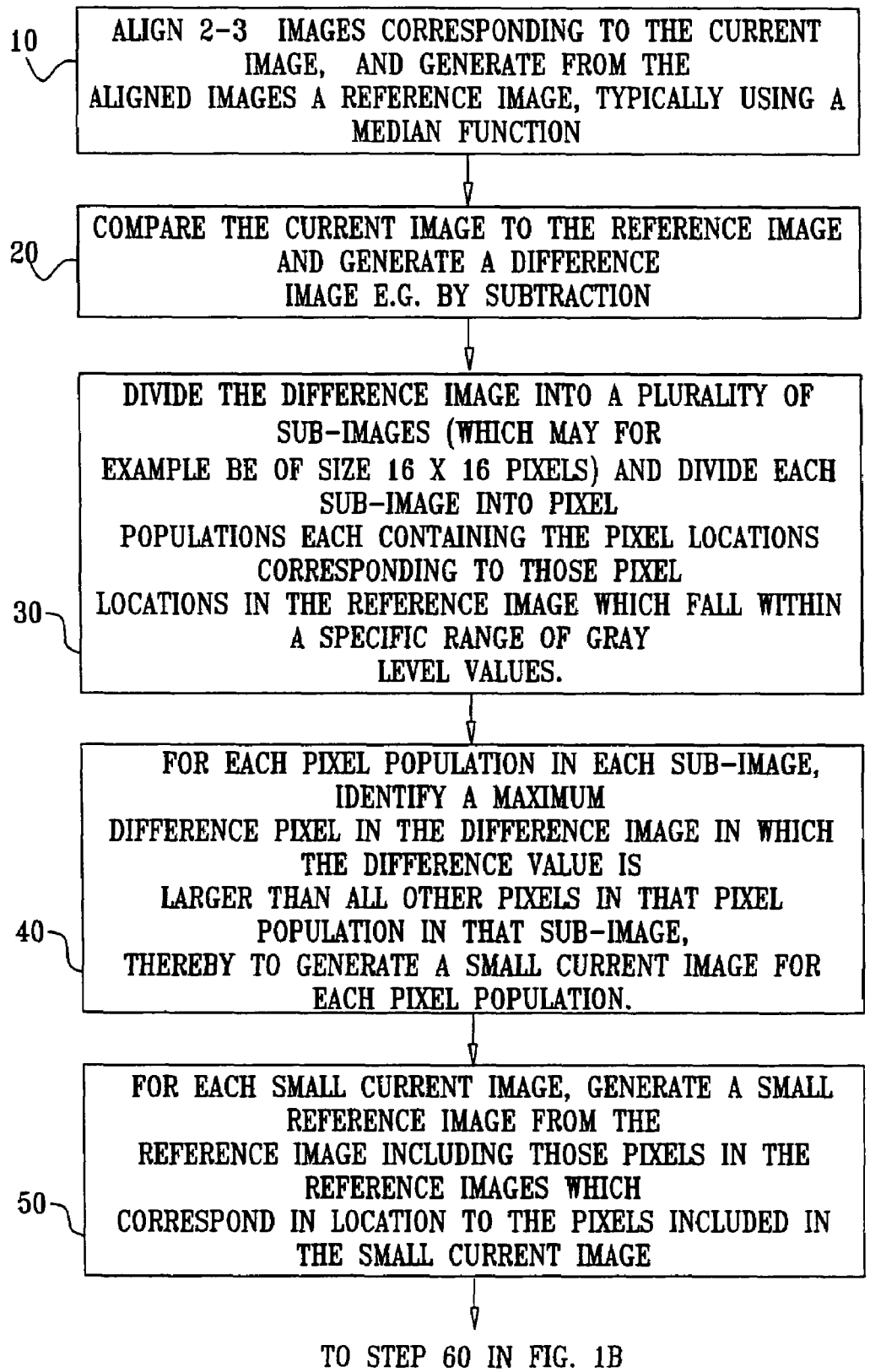

Reference is now made to FIGS. 1A-1B which, taken together, are a simplified flowchart illustration of a preferred method for inspecting images of a microscopic object.

In step 10, align 2-3 images corresponding to the current image, and generate from the aligned images a reference image, typically using a median function.

In step 20, compare the current image to the reference image and generate a difference image e.g. by subtraction.

In step 30, divide the difference image into a plurality of sub-images (which may for example be of size 16×16 pixels) and divide each sub-image into pixel populations each containing the pixel locations corresponding to those pixel locations in the reference image which fall within a specific range of gray level values.

Typically, the user is prompted to select "bins", by selecting two or more ranges of gray level values to be grouped together. Typically, the user selects gray level ranges which best represent the clustering of gray level values in a particular image. For example, a particular image may appear to the eye to include five "clusters" of gray. The user may employ a gray level histogram of the image to identify the gray level values associated with each cluster.

In step 40, for each pixel population in each sub-image, identify a maximum difference pixel in the difference image in which the difference value is larger than all other pixels in that pixel population in that sub-image, thereby to generate a small current image for each pixel population.

Each small current image contains a number of pixels corresponding to the number of pixels in each sub-image.

In step 50, for each small current image, generate a small reference image from the reference image including those pixels in the reference images which correspond in location to the pixels included in the small current image.

In step 60, for each small current image, select at least one predetermined set of (e.g. 4-40) maximal maximum difference pixels comprising small current image pixels which are locally (in which case several sets are defined) or globally (in which case a single set is defined) maximal where local maximality is determined for each slice of gray levels (gray level bin) within the small reference image. The output of this step is sets (one set per small current image, if maximal maximum difference pixels are determined globally, and several sets per small current image if maximal maximum difference pixels are determined locally) of locations of possible defects ("alarms").

In step 70, threshold the alarms so as to filter out individual alarms whose values in the difference image are low relative to the values of the non-alarm pixels in that slice of the difference image whose gray levels, in the original image, are similar to the gray levels, in the original image, of the individual alarm and so as to retain individual alarms whose values in the difference image are high relative to the values of the non-alarm pixels in that slice of the difference image whose gray levels, in the reference image, are similar to the gray levels, in the reference image, of the individual alarm.

Figure 2B:
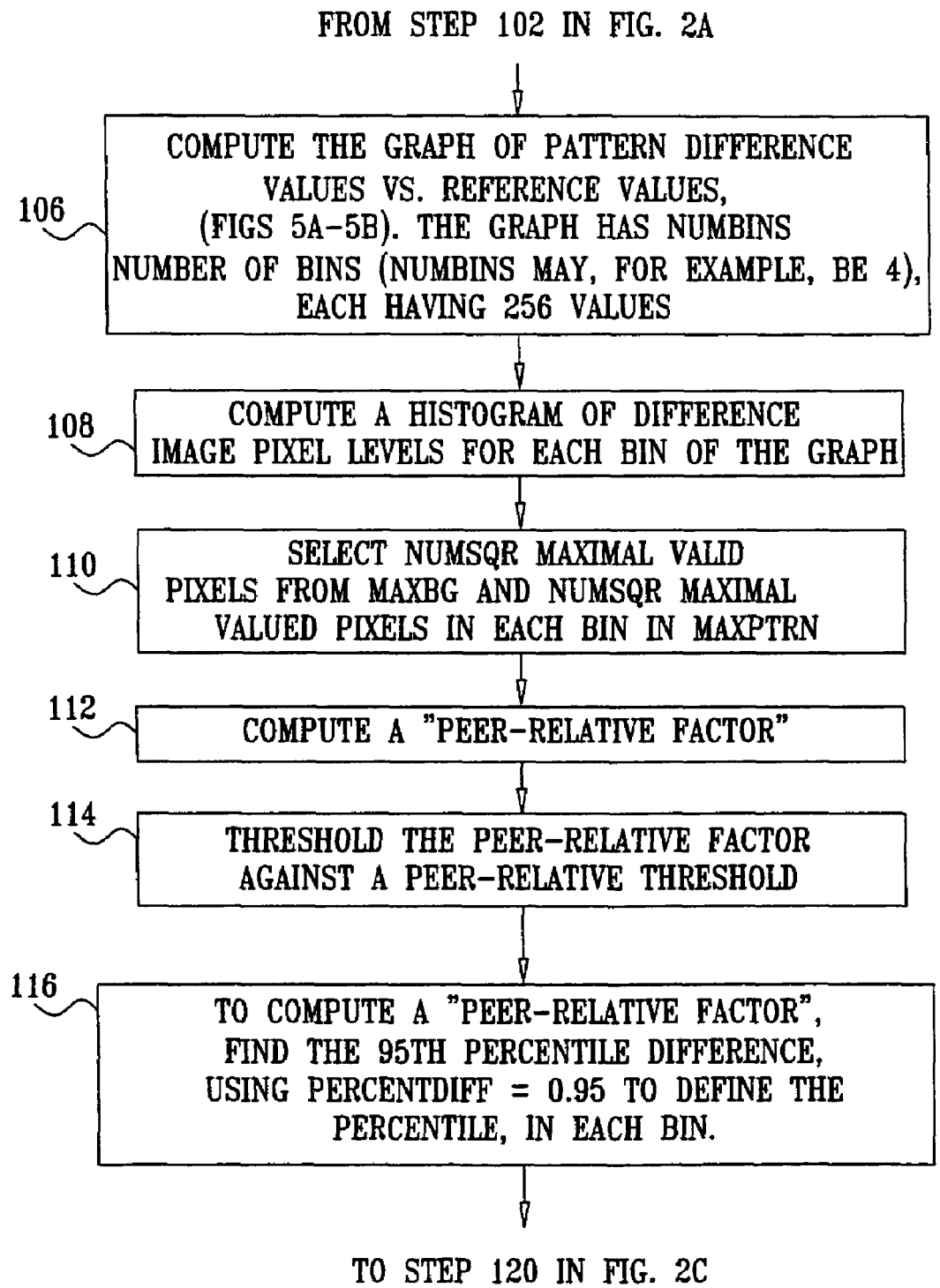
Figure 2C:
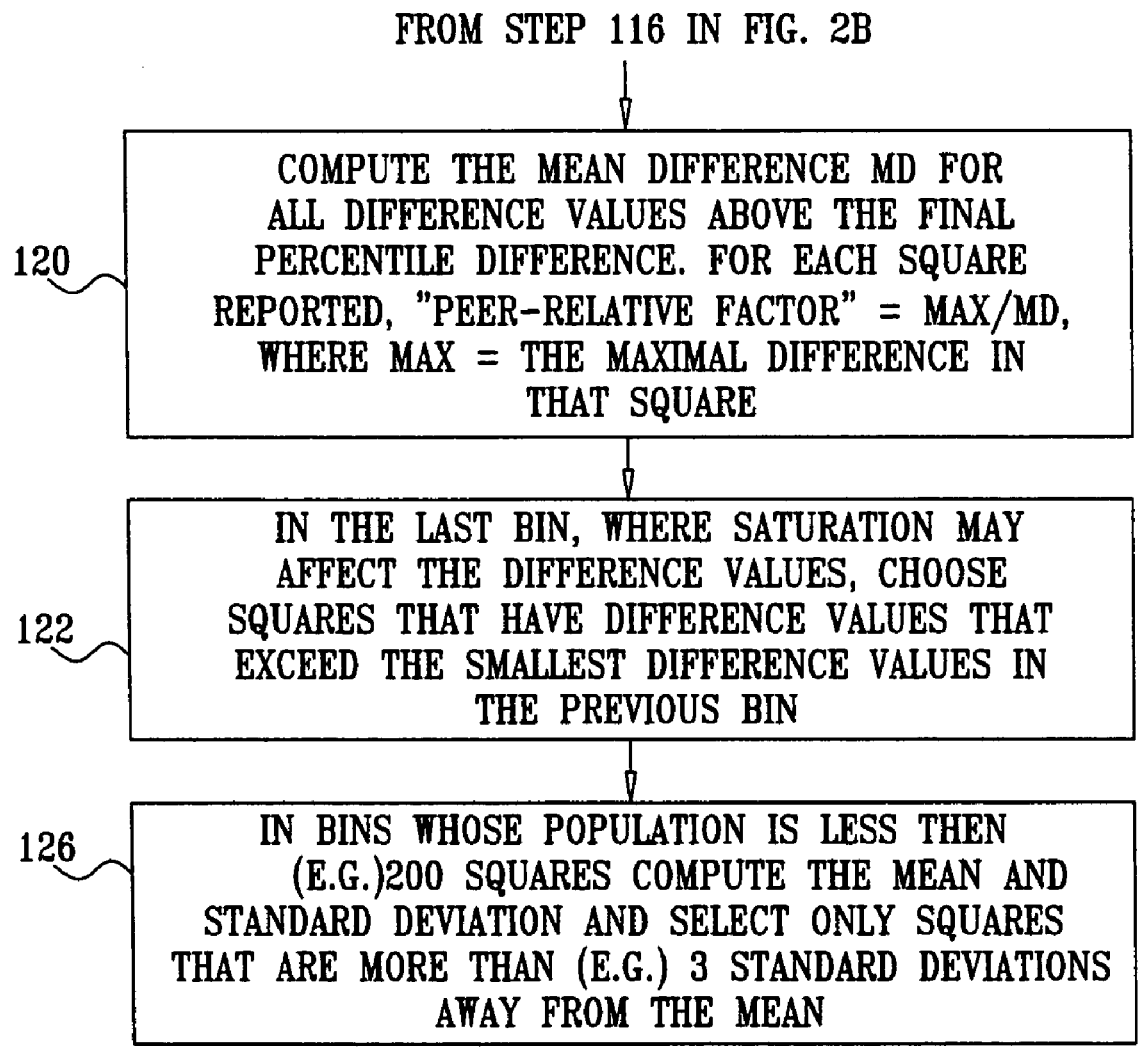

Reference is now made to FIGS. 2A-2C, which together form a preferred implementation of the method of FIGS. 1A-1B. In FIGS. 2A-2C, maximal differences are found, and comparisons are then made. Selection of defects uses a peer-relative threshold, which changes according to sensitivity.

Figure 3:
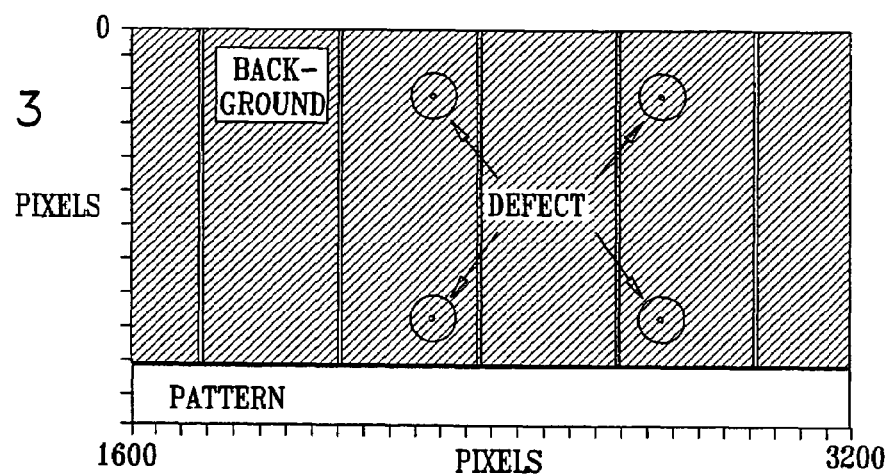
FIG. 3 is an example of an image which may be input to the method of FIGS. 1A-2C.

The process of finding maximal differences, in the implementation of FIGS. 2A-2C, preferably comprises the following steps: In step 82, input three images I1, I2, I3. An example of such an image is illustrated in FIG. 3. The example image of FIG. 3 has four defects. In step 84, perform re-sampling of two images IR1, IR2 so that they will match the third image I3, preferably as described herein with reference to FIG. 13. In step 86, compute the median image M of the two re-sampled images and the original image. In step 88, compute three difference images, D1, D2 and D3, between IR1, IR2, and I3 respectively and the median image M.

For each difference image (D1, D2, D3), in step 94, divide the image by a grid of 16×16 pixels. In step 96, exclude squares that are in dead regions. "Dead regions" are regions of the image that are black or very dark due to artifactual characteristics of the imaging equipment such as defective CCD (charge-coupled device) pixels and foreign particles trapped along the optical path. In step 98, for each square, categorize the pixels as pattern pixels and background pixels by thresholding with a parameter, Tpeak. The Tpeak parameter may be defined in a system configuration file. Tpeak may, for example, be defined as a gray level value between 20 and 40.

Figure 4A:
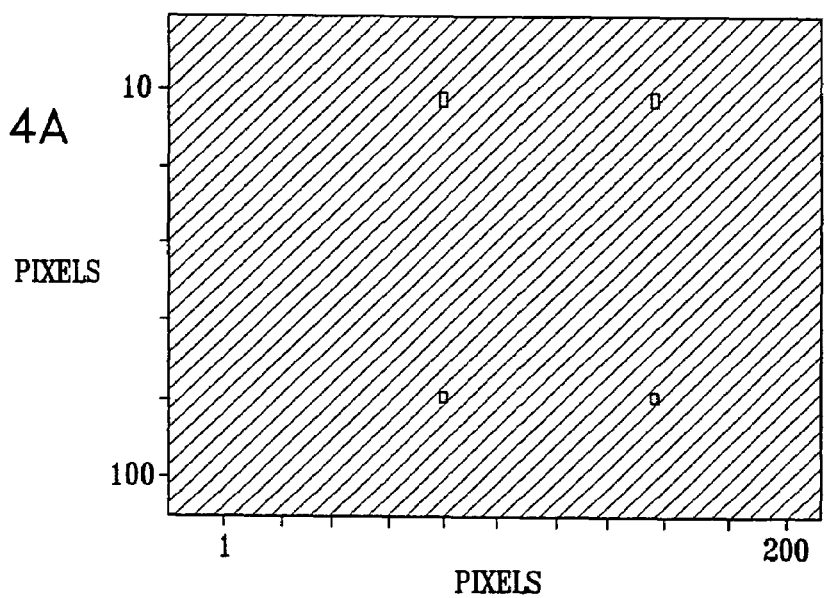
FIG. 4A is a small image, generated from FIG. 3, of maximal differences found in the background as described in FIG. 2A, step 100.

In step 100, for each square, find the maximal difference value for the background pixels. Put all the maximal differences in a new small image, MAXBG. A MAXBG image which might be generated for the example image of FIG. 3 is illustrated in FIG. 4A. As shown, due to the fact that the background is treated separately from the pattern, the four defects which are all defects in the background are easily apparent in the maximal difference background image of FIG. 4A, even though the difference values of these defects are not significantly different from the difference values of the pattern.

Figure 4B:
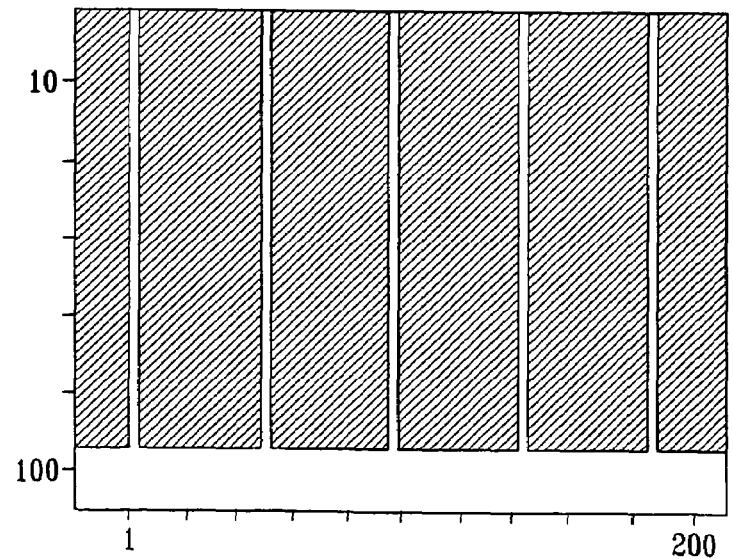
FIG. 4B is a small image, generated from FIG. 3, of maximal differences found in the pattern as described in FIG. 2A, step 102.

In step 102, for each square, find the maximal difference value for the pattern pixels. Put all the maximal differences in a new small image MAXPTRN. Continuing the example of FIGS. 3-4A, the pattern maximal differences are shown in FIG. 4B.

Figure 5A:
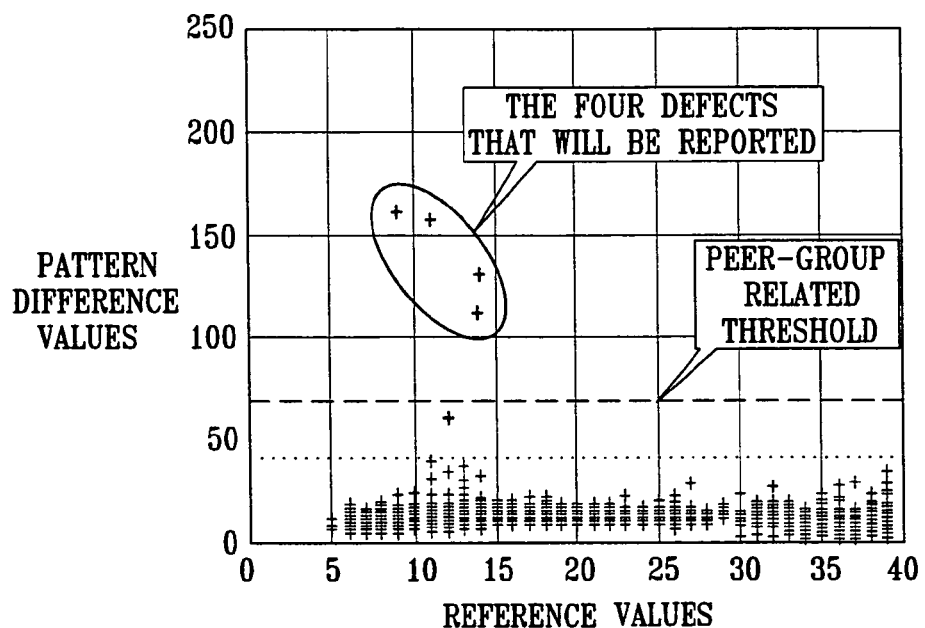
FIGS. 5A and 5B are examples of graphs to be used for analyzing the images of FIGS. 3, 4A, and 4B in the implementation of FIGS. 2A-2C.
Figure 5B:
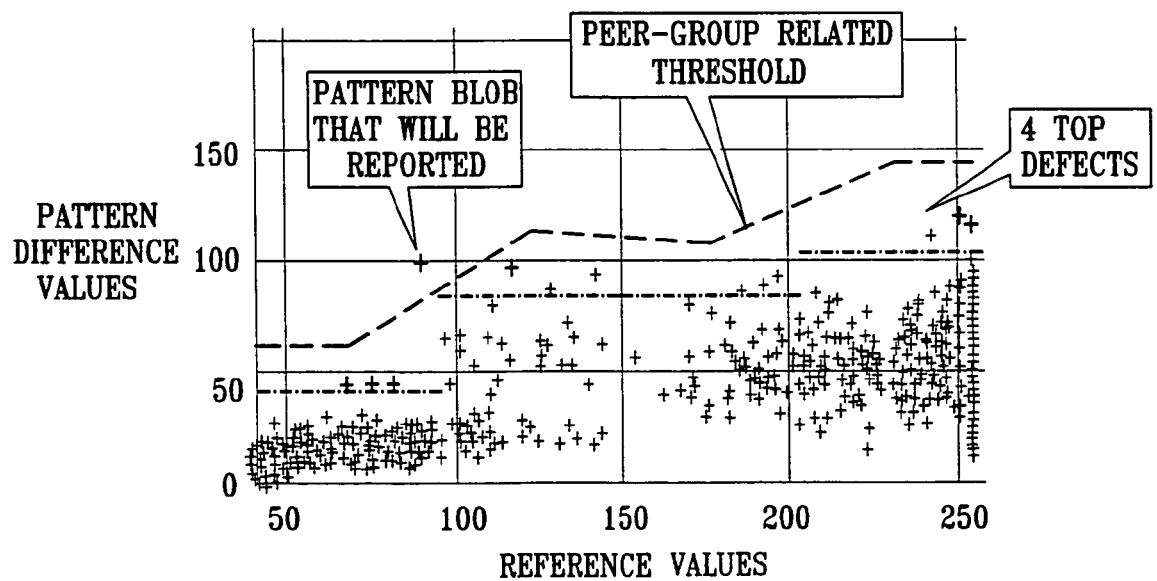

In step 106, compute the graph of pattern difference values vs. reference values, i.e. graph the maximal difference values in the image being analyzed, with the gray level values of the same locations in the reference image. Continuing the example of FIGS. 3-4B, an example graph is shown in FIGS. 5A and 5B, taken together. The graph has NumBins number of bins (NunBins may, for example, be 4), each having 256 values. FIG. 5A shows the graph for the background pixels (reference image gray level values of 0-40). As shown, the four background defects of FIG. 3 are far above all other points on the graph. FIG. 5B shows the graph for the pattern pixels (reference image gray level values of 50-250). In FIG. 5B, four bins or gray level slices are defined (50-100, 100-150, 150-200, 200-255 respectively) and three maximal maximal-value difference pixels are selected per bin i.e. 12 maximal maximal-value difference pixels which are locally maximal may be selected.

In step 108, compute a histogram of difference image pixel levels for each bin of the graph.

In step 110, take NumSqr pixels from MAXBG and NumSqr pixels in each bin in MAXPTRN with maximal values. In step 112, compute a "peer-relative factor" as described below and, in step 114, threshold the peer-relative factor against a peer-relative threshold. In step 116, to compute a "peer-relative factor", the parameter PercentDiff=0.95 may be employed. Find the percentile difference, using PercentDiff to define the percentile, in each bin. In other words, find the difference value in each bin that is higher than PercentDiff (e.g. 95%) of the difference values in that bin. In step 120, compute the mean difference MD for all difference values above the percentile difference. For each square reported, the "peer-relative factor" equals the maximal difference in that square, divided by MD.

In step 122, in the last bin, where saturation may affect the difference values, choose squares that have difference values that exceed the smallest difference values in the previous bin. In step 126, in bins whose population is less then 200 squares, compute the mean and standard deviation and select only squares that are more than 3 standard deviations away from the mean.

The implementation of FIGS. 2A-2C is also useful for comparing I>3 images, except that the reference image is generated as follows: If I is odd, each pixel in the reference image is the median value of the I pixels in corresponding locations in the I images. If I is even each pixel in the reference image is the average of the two middle values from among the I pixels in corresponding locations in the I images.

FIGS. 3-5B are examples of input to the method of FIGS. 1A-2C and intermediate work products generated thereby. Specifically, FIG. 3 is an example of an image which may be input to the method of FIGS. 1A-2C. FIG. 3 is an image containing four defects which are to be found. FIG. 4A is a small image, generated by the method of FIGS. 1A-2C from the image of FIG. 3, representing maximal differences found in the background of the-image as described in FIG. 2A, step 100. All four defects of FIG. 3 appear in FIG. 4A, which is expected, since all four are background defects rather than pattern defects. FIG. 4B is a small image, generated from FIG. 3, of maximal differences found in the pattern of the image of FIG. 3, as described in FIG. 2A, step 102. The four defects do not appear in FIG. 4A, as expected. As shown, the difference image, in patterned areas, is almost always non-zero because the patterned areas are typically noisy except in areas where the pattern is saturated (uniformly maximal in value, e.g. 255 gray levels).

FIGS. 5A-5B, taken together, form a graph of maximal pattern difference values for one of the 3 (e.g.) input images, vs. corresponding reference values. Specifically, as described herein, the input image has been divided into squares of size 16 pixels×16 pixels. The graph shows one, maximal, difference value (designated by a "+") for each "bin" defined within each such 16-pixel×16-pixel square. Therefore, the number of +'s in the graph is (number of squares)×(number of bins per square). Also shown is the defect filtering threshold, which in FIG. 5A is seen to be approximately 70 gray levels for the background bin, and in FIG. 5B is seen to increase for the various pattern bins. Typically, a continuous linear function is used to define the threshold over the various pattern bins as shown in FIG. 5B.

Figure 6B:
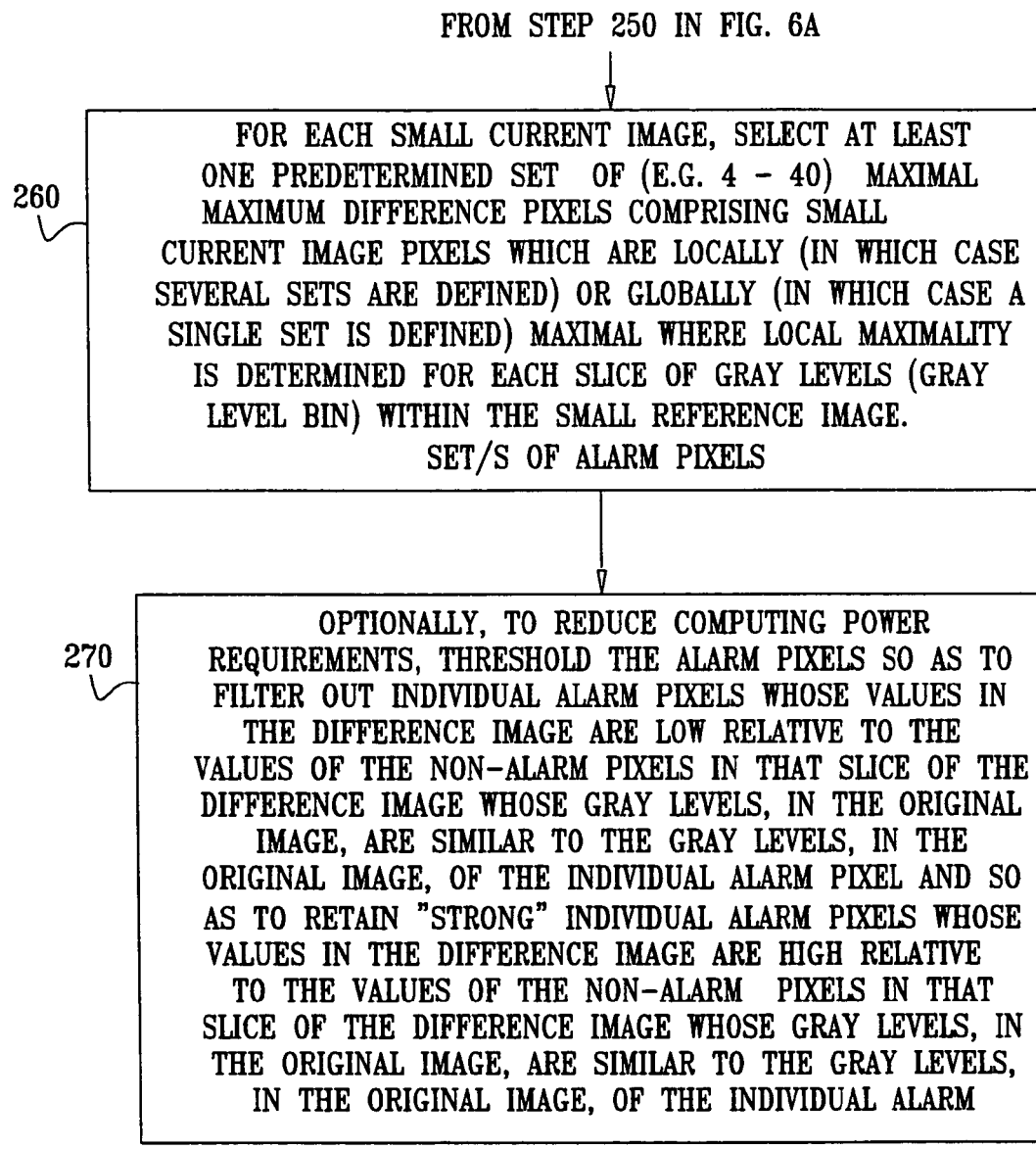

Reference is now made to FIGS. 6A-6B which, taken together, are an image inspection method operative in accordance with a preferred embodiment of the present invention, and which is particularly suitable for inspecting images of dark-field illuminated objects.

In step 210, align n images (n=2 or 3, e.g.) corresponding to the current image, and generate, typically from the n aligned images, a reference image, typically using a pixel-level median function.

In step 220, compare the current image to the reference image and generate a difference image e.g. by subtraction.

In step 230, divide the difference image into a plurality of sub-images and divide each sub-image into pixel populations each containing the pixel locations corresponding to those pixel locations in the reference image which fall within a specific range of gray level values.

In step 240, for each pixel population in each sub-image, identify a maximum difference pixel in the difference image in which the difference value is larger than all other pixels in that pixel population in that sub-image, thereby to generate a small current image for each pixel population.

In step 250, for each small current image, generate a small reference image from the reference image including those pixels in the reference images which correspond in location to the pixels included in the small current image.

In step 260, for each small current image, select at least one predetermined set of (e.g. 4-40) maximal maximum difference pixels comprising small current image pixels which are locally (in which case several sets are defined) or globally (in which case a single set is defined) maximal where local maximality is determined for each slice of gray levels (gray level bin) within the small reference image. The output of this step is sets (one set per small current image, if maximal maximum difference pixels are determined globally and several sets per small current image, if maximal maximum difference pixels are determined locally) of locations of possible defect pixels ("alarm pixels").

In step 270, optionally, to reduce computing power requirements, threshold the alarm pixels so as to filter out individual alarm pixels whose values in the difference image are low relative to the values of the non-alarm pixels in that slice of the difference image whose gray levels, in the original image, are similar to the gray levels, in the original image, of the individual alarm pixel and so as to retain "strong" individual alarm pixels whose values in the difference image are high relative to the values of the non-alarm pixels in that slice of the difference image whose gray levels, in the original image, are similar to the gray levels, in the original image, of the individual alarm.

It is appreciated that steps 210-270 may be the same as steps 10-70 in FIGS. 1A-1B. It is further appreciated that steps 10-70 or steps 210-270 may be employed for dark field illuminated objects as well as bright field illuminated objects, both in die-to-die type inspections and in cell-to-cell type inspections, and even for bare-mode type inspections. Bare-mode type inspections are described hereinbelow with reference to FIGS. 8A-8B.

Figure 7:
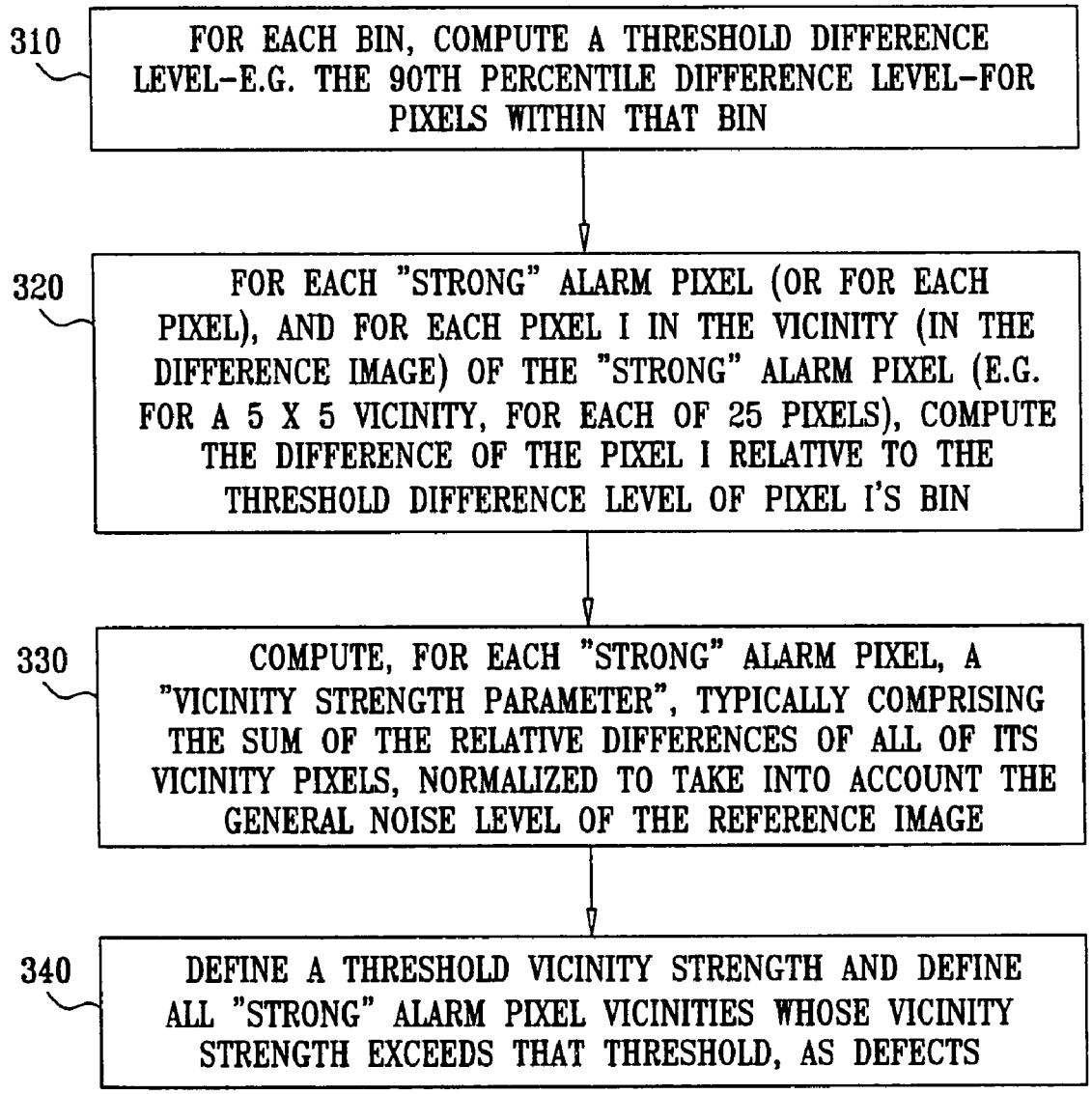
FIG. 7 is a simplified flowchart illustration of a preferred method for performing step 270 of FIG. 6B.

FIG. 7 is a preferred method for performing step 270, wherein the vicinity (in the difference image) of each "strong" alarm pixel (or, preferably, of all alarm pixels) is inspected to determine whether the vicinity as a whole comprises large differences relative to the reference-to-image differences found for similar gray level values in the reference image.

In step 310, for each bin, compute a threshold difference level—e.g. the 90th percentile difference level—for pixels within that bin.

In step 320, for each "strong" alarm pixel (or for each pixel), and for each pixel i in the vicinity (in the difference image) of the "strong" alarm pixel (e.g. for a 5×5 vicinity, for each of 25 pixels), compute the difference of the pixel i relative to the threshold difference level of pixel i's bin.

In step 330, compute, for each "strong" alarm pixel, a "vicinity strength parameter", typically comprising the sum of the relative differences of all of its vicinity pixels, normalized to take into account the general noise level of the reference image.

A preferred method for computing vicinity strength (VS) is now described. The vicinity strength, according to a preferred embodiment of the present invention, is:

$$VS = \frac{\left|\sum_i \frac{(I-R)_i}{N_i^2}\right|}{\sqrt{\sum_i \frac{1}{N_i^2}}}$$

where i is an index over the pixels in the vicinity (e.g. 5×5 vicinity) of the "peak" of the defect, the "peak" of the defect is the pixel in the defect having the largest difference value, I-R is the difference image, and $N_i$ is the noise estimate of the bin to which the i'th pixel belongs which may be computed as the 90th percentile (almost largest) difference value in the bin to which the i'th pixel belongs.

In step 340, define a threshold vicinity strength, and define all "strong" alarm pixel vicinities whose vicinity strength exceeds that threshold, as defects.

Figure 8A:
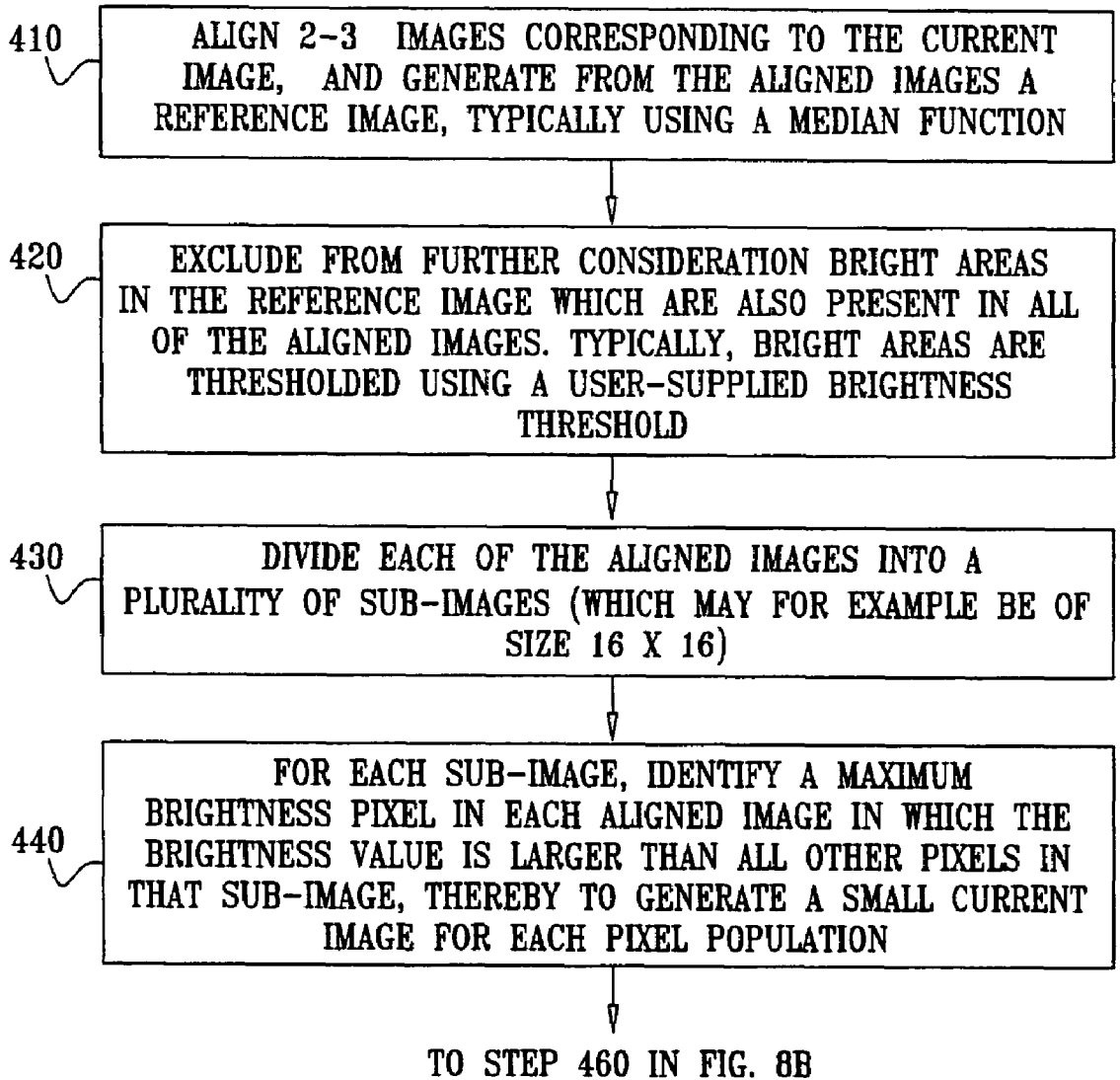

Reference is now made to FIGS. 8A-8B which, taken together, form a simplified flowchart of a preferred method of inspection particularly useful when it is known in advance that a wafer image is, other than defects, black—for example, because in a certain area the wafer is bare, having no pattern, or because the wafer or an area therein has a known pattern which was filtered out, using a Fourier filter or other suitable means, in order to prevent the pattern from interfering with a defect detection process sensitive to that pattern. In these situations, bare mode inspection may be used, as described in detail herein with reference to FIGS. 8A-8B.

In bare mode inspection, dark field illumination is employed. Instead of working on the difference image (image-reference) as in the dark field inspection shown and described herein, do as follows:

a. Use the reference image; however, remove from consideration all non-defective bright areas. These are bright areas appearing in all images and are assumed to be areas that could not be filtered out and not defects. This is done by filtering pixels in the reference image that are brighter than a threshold.

b. For all other areas, defect candidates, rather than being the largest found differences, are the brightest pixels. The inspection method then proceeds as described above for dark-field inspection. Specifically, bare mode inspection may comprise the following steps, as shown in FIGS. 8A-8B:

In step 410, align 2-3 images corresponding to the current image, and generate from the aligned images a reference image, typically using a median function.

In step 420, exclude from further consideration bright areas in the reference image which are also present in all of the aligned images. Typically, bright areas are thresholded using a user-supplied brightness threshold. Typically, the reference image, in bare mode, is used only to perform step 420 and is not used thereafter.

Steps 430 onward are typically performed for the aligned images, one at a time, i.e. all of these steps are performed first for the first aligned image, then for the second aligned image, and so on.

In step 430, divide each of the aligned images into a plurality of sub-images (which may for example be of size 16×16).

In step 440, for each sub-image, identify a maximum brightness pixel in each aligned image in which the brightness value is larger than all other pixels in that sub-image, thereby to generate a small current image for each pixel population.

In step 460, for each small current image, select at least one predetermined set of (e.g. 4-40) maximal maximum brightness pixels comprising small current image pixels which are locally (in which case several sets are defined) or globally (in which case a single set is defined) maximal, where local maximality is determined for each slice of gray levels (gray level bin) within the small reference image. The output of this step is sets (one set per small current image, if maximal maximum brightness pixels are determined globally, and several sets per small current image, if maximal maximum brightness pixels are determined locally) of locations of possible defect pixels ("alarm pixels").

In step 470, optionally, to reduce computing power requirements, threshold the alarm pixels so as to filter out individual alarm pixels whose values in the current aligned image are low relative to the values of the non-alarm pixels and so as to retain "strong" individual alarm pixels whose values in the current aligned image are high relative to the values of the non-alarm pixels.

In step 510, compute a threshold brightness level—e.g. the 90th percentile brightness level—for pixels within that aligned image.

In step 520, compute, for each "strong" alarm pixel, a "vicinity strength parameter", typically comprising the sum of the brightnesses of all of its vicinity pixels (e.g. the 5×5 pixels surrounding it), normalized to take into account the general noise level of the current aligned image.

In step 530, define a threshold vicinity strength and define all "strong" alarm pixel vicinities whose vicinity strength exceeds that threshold, as defects.

Figure 9:
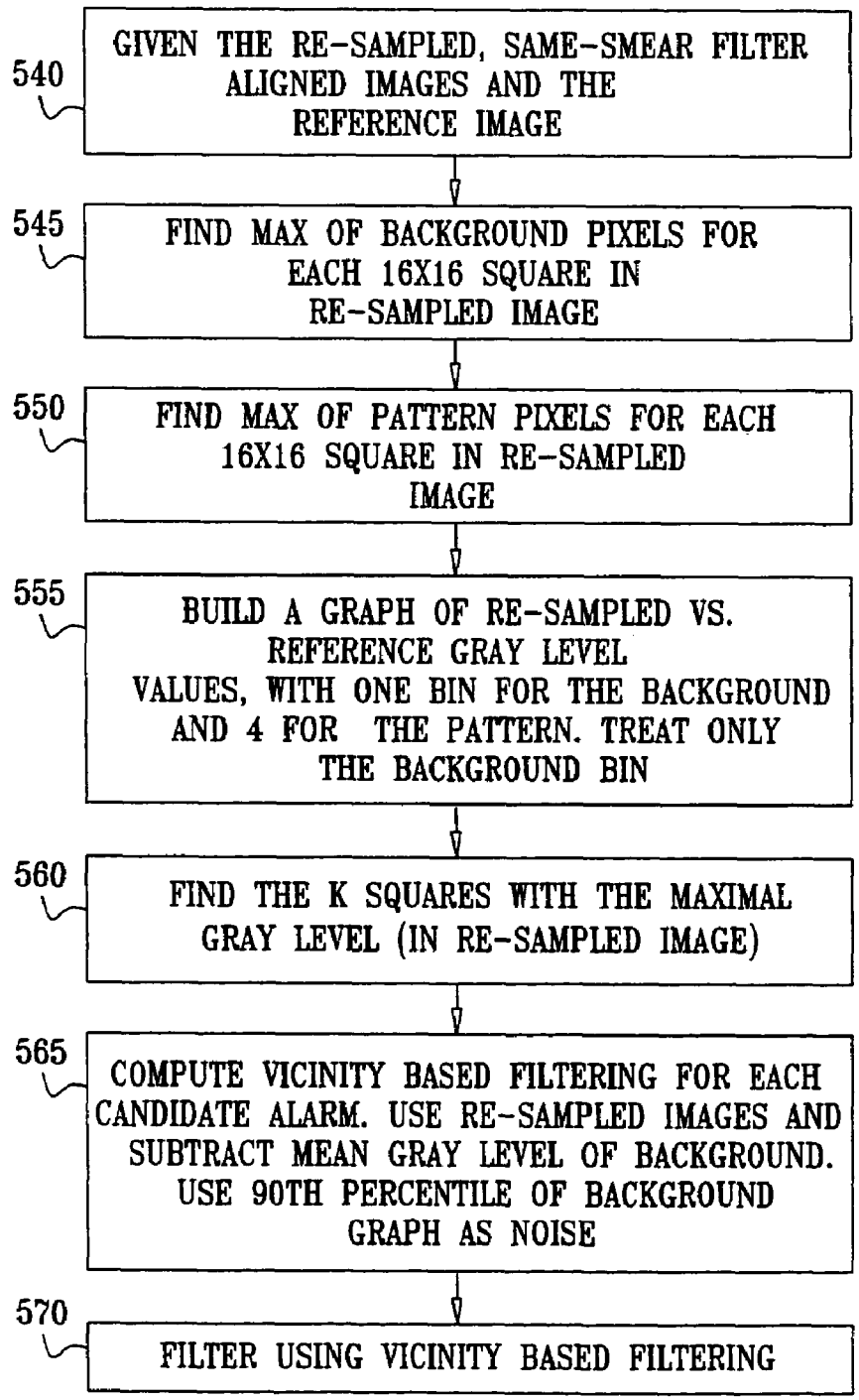
FIG. 9 is a simplified flowchart illustration of a preferred implementation of the bare mode inspection method of FIGS. 8A-8B.

Reference is now made to FIG. 9, which is a preferred implementation of the bare mode inspection method of FIGS. 8A-8B.

In step 540, given the re-sampled, same-smear filter aligned images and the reference image, in step 545, find a maximum of background pixels for each 16×16 square in the re-sampled image.

In step 550, find a maximum of pattern pixels for each 16×16 square in the re-sampled image.

In step 555, build a graph of re-sampled vs. reference gray level values, with one bin for the background and four for the pattern. Treat only the background bin.

In step 560, find the k squares with the maximal gray level (in the re-sampled image).

In step 565, compute vicinity-based filtering for each candidate alarm. Use re-sampled images and subtract the mean gray level of the background. Use the $90^{th}$ percentile of the background graph as noise.

In step 570, filter using vicinity-based filtering.

Figure 10A:
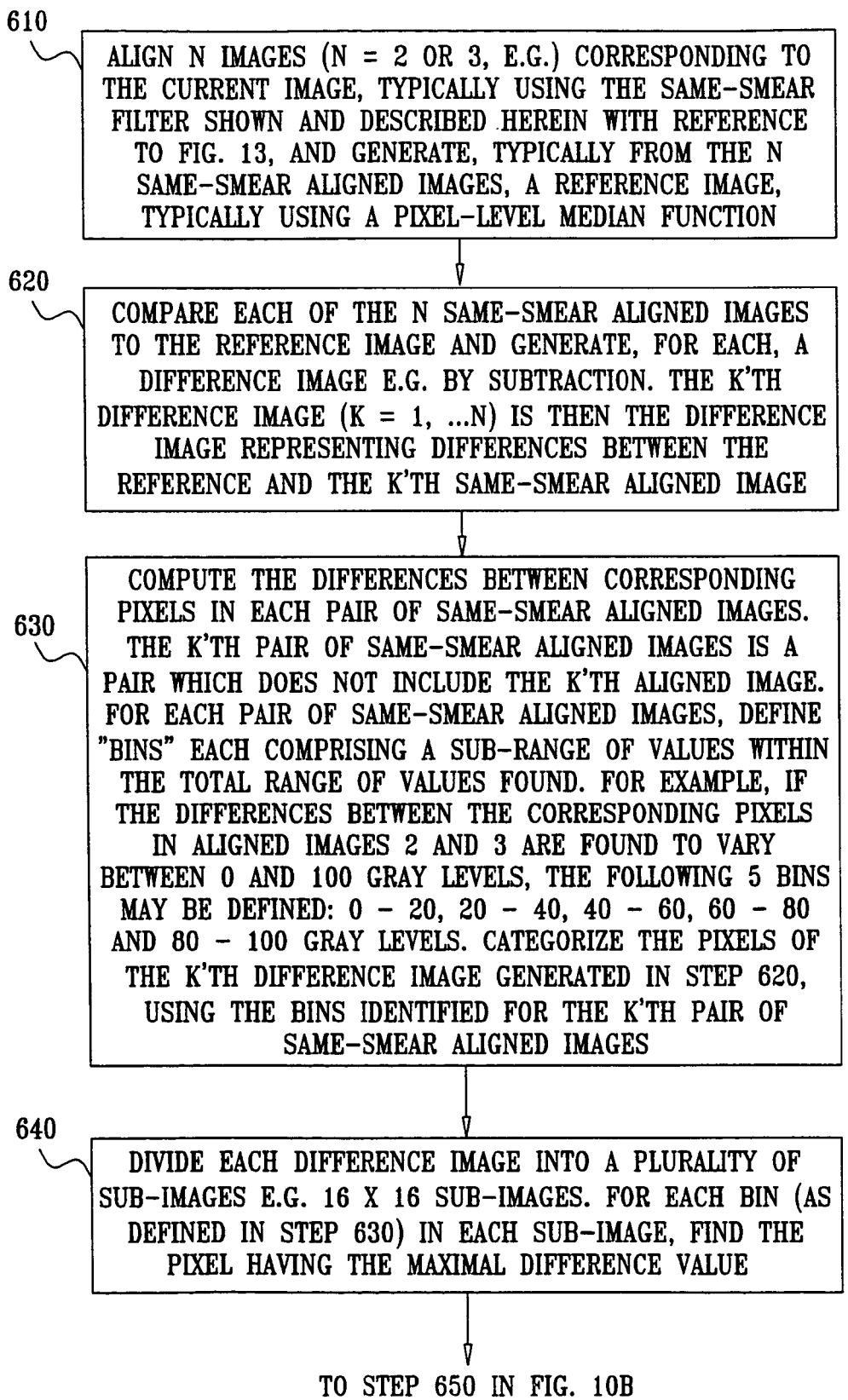

Reference is now made to FIGS. 10A-10B which, taken together, are an image inspection method operative in accordance with a preferred embodiment of the present invention, and which is particularly suitable for performing die-to-die inspection of images of bright-field illuminated objects.

Figure 13:
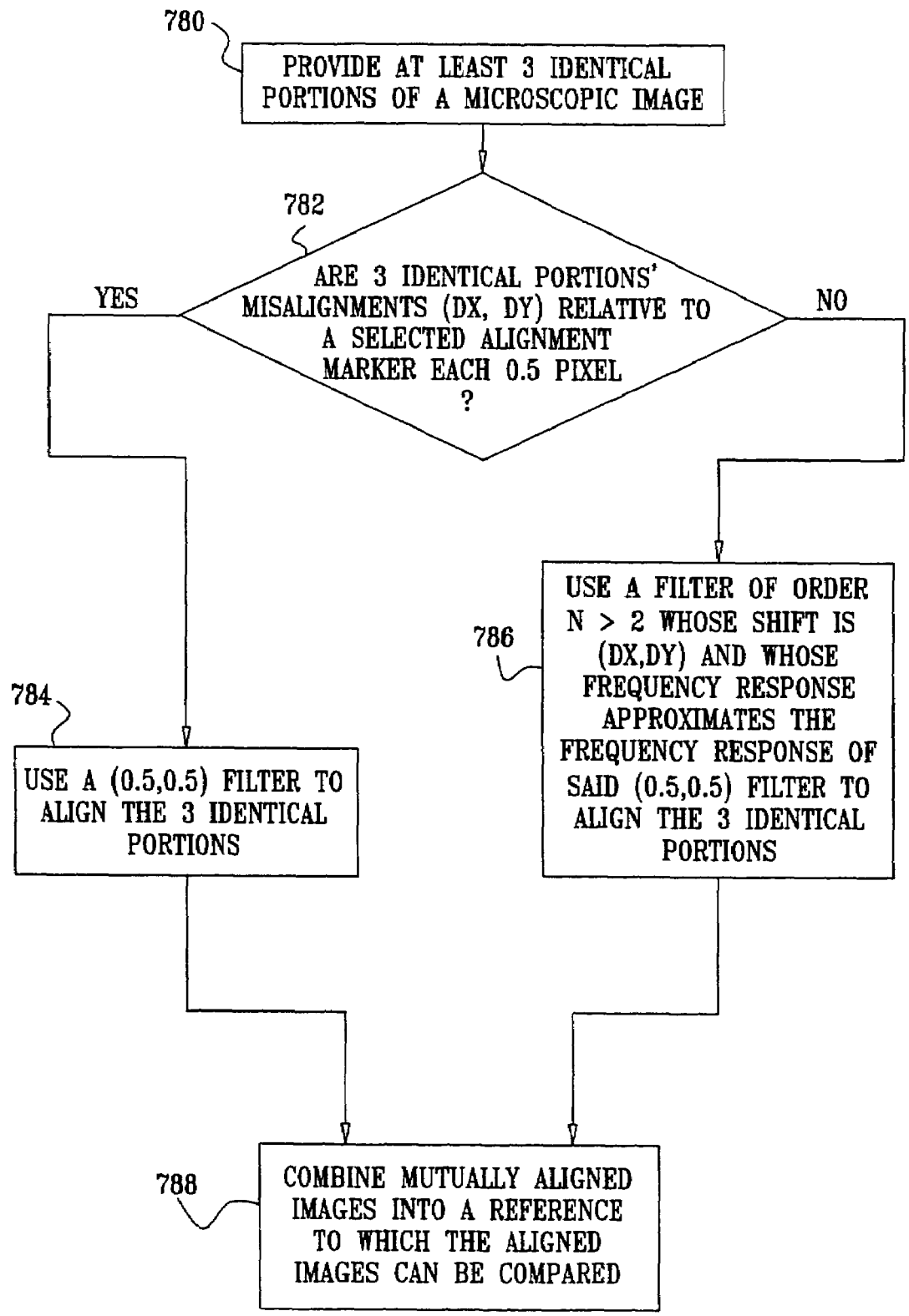
FIG. 13 is a simplified flowchart illustration of preferred method for generating and using a same-smear filter to provide several aligned images having the same smear.

In step 610, align n images (n=2 or 3, e.g.) corresponding to the current image, typically using the same-smear filter shown and described herein with reference to FIG. 13, and generate, typically from the n same-smear aligned images, a reference image, typically using a pixel-level median function.

In step 620, compare each of the n same-smear aligned images to the reference image and generate, for each, a difference image e.g. by subtraction. The k'th difference image (k=1, . . . n) is then the difference image representing differences between the reference and the k'th same-smear aligned image.

In step 630, compute the differences between corresponding pixels in each pair of same-smear aligned images. The k'th pair of same-smear aligned images is a pair which does not include the k'th aligned image. For each pair of same-smear aligned images define "bins" each comprising a sub-range of values within the total range of difference values found. For example, if the differences between the corresponding pixels in aligned images 2 and 3 are found to vary between 0 and 100 gray levels, the following 5 bins may be defined: 0-20, 20-40, 40-60, 60-80 and 80-100 gray levels. Categorize the pixels of the k'th difference image generated in step 620, using the bins identified for the k'th pair of same-smear aligned images.

In step 640, divide each difference image into a plurality of sub-images e.g. 16×16 sub-images. For each bin (as defined in step 630) in each sub-image, find the pixel having the maximal difference value.

In step 650, generate a small image for each bin, including only those maximal difference values i.e. containing only one pixel per sub-image. If a bin is not represented in a particular sub-image, the pixel corresponding to that sub-image in that bin's small image is typically given a value of 0.

Figure 11:
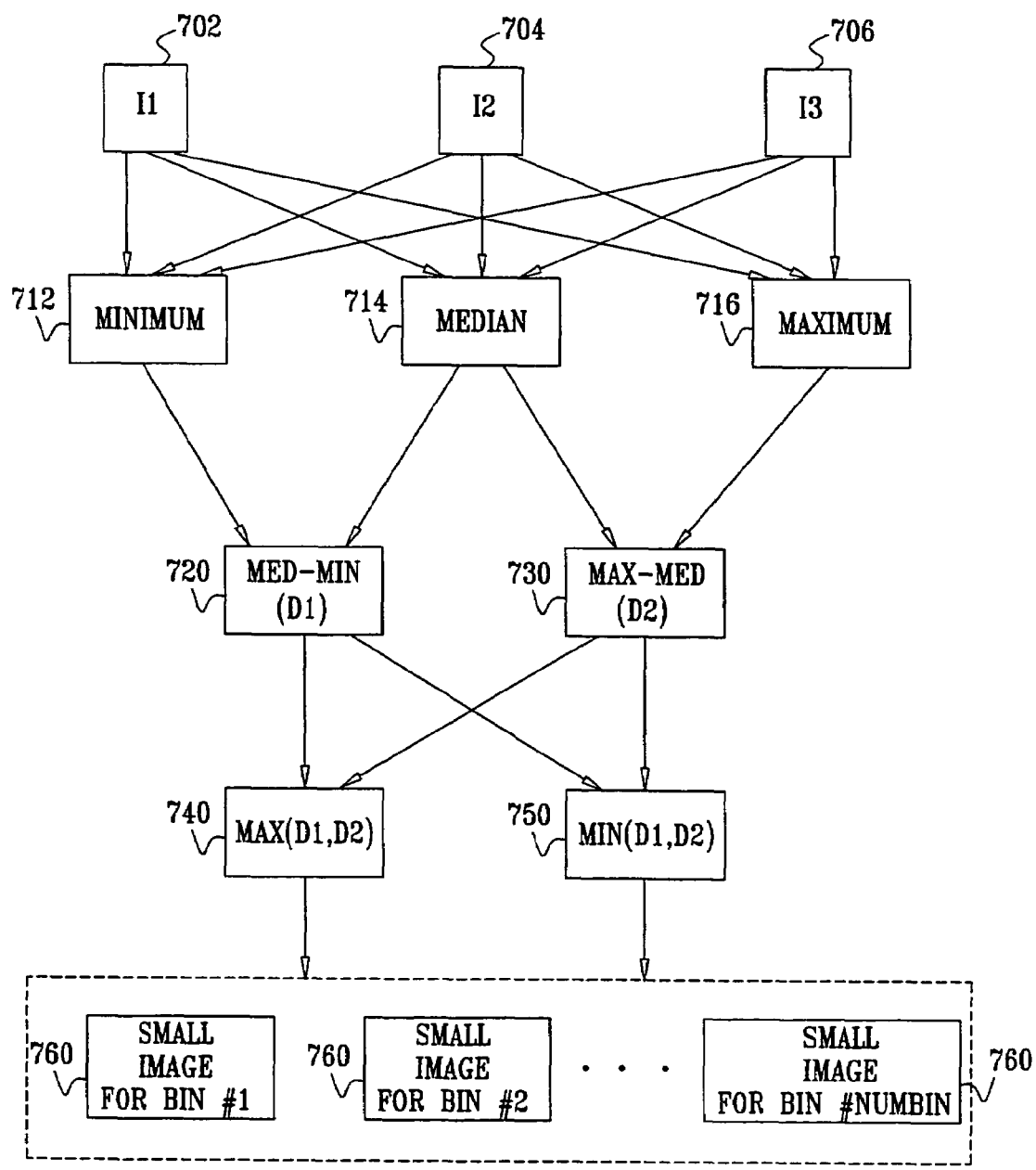
FIG. 11 is a diagram illustrating an alternative to the method described in step 650 of FIG. 10B, for generating a small image for each of a plurality of bins.

Alternatively, as shown in FIG. 11, the small image for each bin may be generated as follows: the n same-smear aligned images generated in step 610 (indicated in FIG. 11 by reference numerals 702, 704 and 706) are sorted, pixel by pixel, so as to generate three new images, indicated in FIG. 11 by reference numerals 712, 714, and 716. The first, minimum image 712 comprises, at each pixel location, the smallest pixel value from among the values of I1, I2 and I3 at that pixel location. The second, median image 714 comprises, at each pixel location, the intermediate pixel value from among the values of I1, I2 and I3 at that pixel location. The third, maximum image 716 comprises, at each pixel location, the largest pixel value from among the values of I1, I2 and I3 at that pixel location. Difference images 720 and 730 are then generated by comparing, respectively, images 712 and 714, and images 714 and 716. Maximum and minimum images 740 and 750 are now generated. The first, maximum image 740 comprises, at each pixel location, the larger pixel value from among the values of D1 and D2 at that pixel location. The second, minimum image 750 comprises, at each pixel location, the smaller pixel value from among the values of D1 and D2 at that pixel location.

The small image for each of a plurality of bins, e.g. 5 bins, or more generally, NUMBIN bins, is now computed. First, 5 or, more generally, NUMBIN bins (gray level slices) are defined in image 750. For example, the 5 bins may each comprise the following gray levels: 0-10, 11-20, 21-30, 31-40, and over 40. For each bin, define a small image 760 as follows: for each image location for which the pixel value in image 750 belongs to the bin, the pixel value of image 760 at that location will be the pixel value of the same location in image 740. For each image location for which the pixel value in image 750 does not belong to the bin, the pixel value of image 760 at that location will be zero.

Returning now to FIG. 10B, in step 660, for each small image, select at least one predetermined set of (e.g. 4-40) maximal maximum difference pixels comprising small image pixels which are locally maximal (in which case several sets are defined) or globally maximal (in which case a single set is defined) where local maximality is determined for each slice of gray levels (gray level bin) within the small reference image. The output of this step is sets (one set per small current image, if maximal maximum difference pixels are determined globally and several sets per small current image, if maximal maximum difference pixels are determined locally) of locations of possible defect pixels ("alarm pixels").

In step 670, optionally, to reduce computing power requirements, threshold the alarm pixels so as to filter out individual alarm pixels whose values in the difference image are low relative to the values of the non-alarm pixels in that slice of the difference image whose gray levels, in the original image, are similar to the gray levels, in the original image, of the individual alarm pixel and so as to retain "strong" individual alarm pixels whose values in the difference image are high relative to the values of the non-alarm pixels in that slice of the difference image whose gray levels, in the original image, are similar to the gray levels, in the original image, of the individual alarm.

Figure 12:
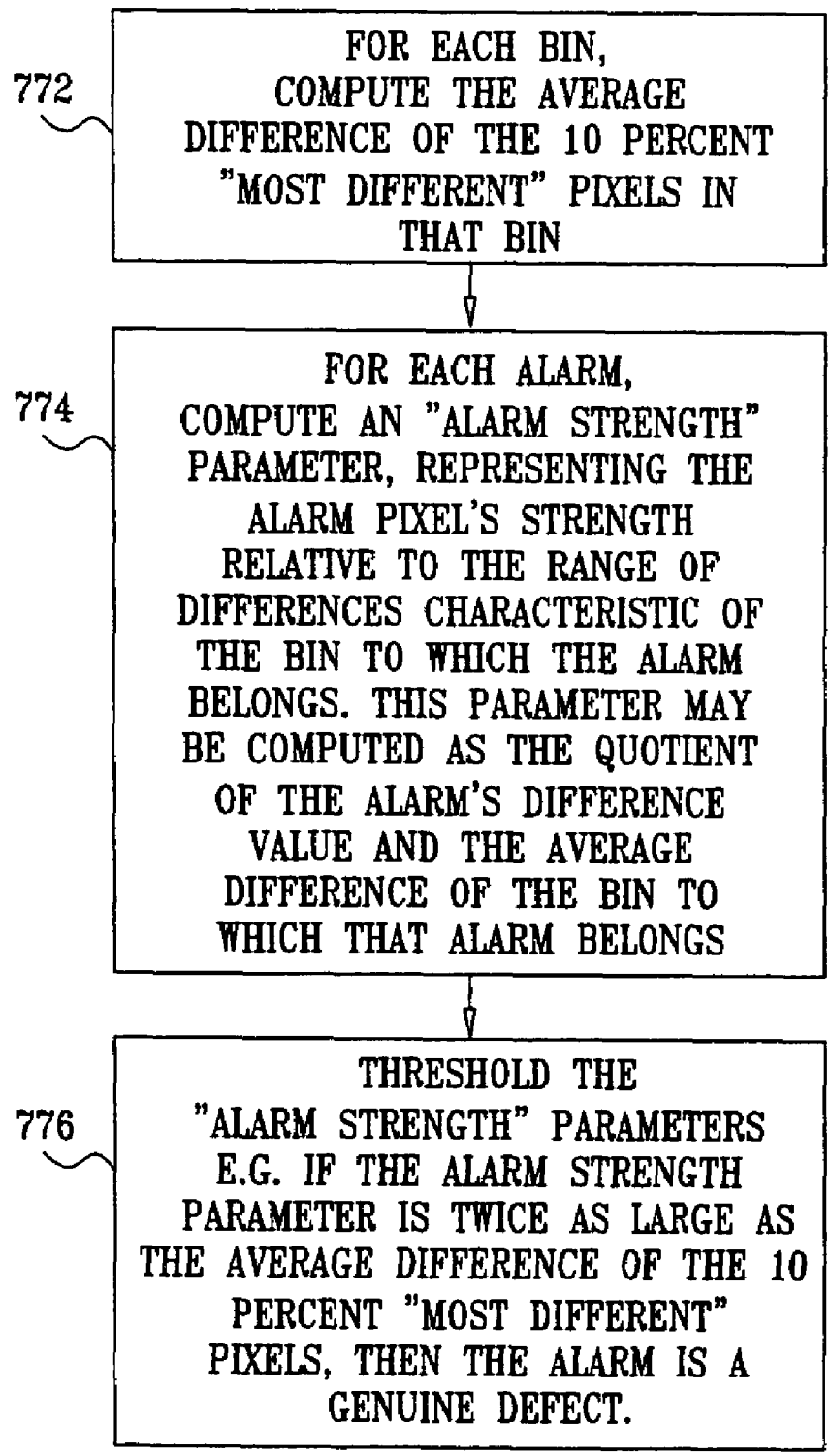
FIG. 12 is a simplified flowchart illustration of a preferred method for performing step 670 of FIG. 10B.

FIG. 12 is a simplified flowchart illustration of a preferred method for performing step 670 of FIG. 10B. The method of FIG. 12 preferably comprises the following steps:

In step 772, for each bin, compute the average difference of the 10 percent "most different" pixels in that bin.

In step 774, for each alarm, compute an "alarm strength" parameter, representing the alarm pixel's strength relative to the range of differences characteristic of the bin to which the alarm belongs. This parameter may be computed as the quotient of the alarm's difference value and the average difference of the bin to which that alarm belongs.

In step 776, threshold the "alarm strength" parameters e.g. if the alarm strength parameter is twice as large as the average difference of the 10 percent "most different" pixels, then the alarm is a genuine defect.

It is appreciated that the peer-group based filtering method described herein in connection with bright field die-to-die or cell-to-cell inspections may alternatively be employed in dark field inspections and even in bare mode inspections. In the peer-group based filtering methods described in detail above, the criterion value used to identify candidate defect pixels or locations is compared, for each candidate defect pixel or location, to the characteristic level of the same value in a peer group defined for each candidate defect pixel or location. The peer group may, for example, comprise the candidate defect pixel/location's vicinity in the reference image, or the candidate defect pixel/location's gray level vicinity. The criterion value may comprise brightness or difference vis-a-vis the reference image or any other suitable criterion value.

Generally, any suitable filtering method may be used in conjunction with any of the defect detection methods shown and described herein, in order to filter out certain defect candidates and remain with a final list of defects. For example, in peer-group based filters constructed and operative in accordance with a preferred embodiment of the present invention, a filtering threshold is typically defined as a function of the distribution (e.g. multiple of the average of the top p percent differences) in the bin to which the "peak" of the defect (the pixel within the defect with the largest difference value) belongs.

In vicinity-strength based filters constructed and operative in accordance with a preferred embodiment of the present invention, a defect candidate is filtered out if the neighboring pixels of the defect candidate's peak, which have certain gray levels, do not seem defective because their differences are not deviant from the expected differences at those gray levels. Typically, defect candidates are filtered out unless each or many of the (e.g. 25) neighboring pixels located in the vicinity of the defect's peak have a high difference value, relative to that neighboring pixel's own bin. Each defect candidate is preferably scored to indicate the extent to which its vicinity has large difference values, largeness typically being defined, for each neighboring pixel, relative to the noise in its own bin, and low-scoring defect candidates are filtered out.

A preferred method for aligning several images of generally the same portion of an object to be inspected is now described. This method is useful in implementing image alignment steps in any of the image inspection methods shown and described herein, such as steps 210, 310, 410 and 610. Typically, the misalignment is only a few pixels in magnitude. Therefore, initially, the images are typically aligned at the whole pixel level, using correlation to compute the correct alignment as described in Jain, pages 400-404. In bright field inspections, linear or non-linear sub-pixel corrections are typically employed. A particularly suitable linear sub-pixel correction filter, computing subpixel x-axis and y-axis shifts dx and dy respectively, comprises the following "same-smear" re-sampling filter:

a. If an image portion's misalignment (dx,dy) relative to a selected alignment marker is 0.5 pixel, using a (0.5,0.5) filter; and
b. otherwise, using a filter of order n>2 whose shift is (dx,dy) and whose frequency response approximates the frequency response of said (0.5,0.5) filter.

Reference is now made to FIG. 13, which is a simplified flowchart illustration of a preferred method for generating and using a same-smear filter to provide several aligned images having the same smear.

In step 780, provide at least three identical portions of a microscopic image.

In step 782, determine whether the three identical portions' misalignments (dx,dy) are each 0.5 pixel relative to a selected alignment marker. If so, proceed to step 784 and use a (0.5,0.5) filter to align the three identical portions. If not, proceed to step 786, and use a filter of order n>2 whose shift is (dx,dy) and whose frequency response approximates the frequency response of the (0.5,0.5) filter to align the three identical portions.

From step 784 or step 786, proceed to step 788, and combine mutually aligned images into a reference to which the aligned images can be compared.

In order to approximate the frequency response of the (0.5,0.5) filter by a higher order filter, relating to a different sub-pixel shift, the following computation may be performed:

$$F(a) = \int_{-\pi}^{\pi} ||H_{0.5}(e^{j\theta})| - |F_0(e^{j\theta})||^2 d\theta$$

where:

$$H_{0.5}(e^{j\theta}) = \frac{1}{2} + \frac{1}{2}e^{-j\theta}, F_0(e^{j\theta})$$

$$= ae^{j\theta} + (1-2a) + ae^{-j\theta} \int_{-\pi}^{\pi} \left|\frac{1}{2} + \frac{1}{2}e^{-j\theta}\right| -$$

$$|ae^{j\theta} + (1-2a) + ae^{-j\theta}|^2 d\theta$$

$$= \int_{-\pi}^{\pi} \left|\left|\frac{1}{2}e^{-j\theta/2} + \frac{1}{2}e^{j\theta/2}\right| - |(1-2a) + a(e^{j\theta} + e^{-j\theta})|\right|^2 d\theta$$

$$= \int_{-\pi}^{\pi} ||\cos\theta| - |(1-2a) + 2a\cos 2\theta||^2 d\theta$$

For $a < \frac{1}{4}$:

$$F(a) = 2(F_1(a) + F_2(a)),$$

where $$F_1(a) = \int_0^{\pi/2} |\cos\theta - (1-2a) - 2a\cos 2\theta|^2 d\theta,$$

$$F_2(a) = \int_{\pi/2}^{\pi} |-\cos\theta - (1-2a) - 2a\cos 2\theta|^2 d\theta$$

$$F_1(a) = \int_0^{\pi/2} |\cos\theta + 2a - 2a\cos 2\theta - 1|^2 d\theta, F_1(a, \theta)$$

$$= \cos\theta + 2a - 2a\cos 2\theta$$

$$\lfloor |F_1(a, \theta) - 1|^2 = |F(a, \theta)|^2 - 2F(a, \theta) + 1^2 \rfloor$$

$$F_1(a) = \int_0^{\pi/2} [|\cos\theta|^2 + |2a - 2a\cos 2\theta|^2 +$$

$$2\cos\theta(2a - 2a\cos 2\theta)] d\theta -$$

$$2\int_0^{\pi/2} (\cos\theta + 2a - 2a\cos 2\theta) d\theta$$

where $$\int_0^{\pi/2} 2a\cos 2\theta d\theta = 0$$

$$F_1(a) = \int_0^{\pi/2} [\cos^2\theta + |2a - 2a\cos 2\theta|^2 +$$

$$2\cos\theta(2a - 2a\cos 2\theta) - 4a - 2\cos\theta] d\theta$$

$$\frac{dF_1(a)}{da} = \frac{\partial}{\partial a}\left[\int_0^{\pi/2} (4a^2 - 8a^2\cos 2\theta + 4a^2\cos^2 2\theta +$$

$$4a\cos\theta - 4a\cos\theta\cos 2\theta - 4a) d\theta\right]$$

$$= 8a\int_0^{\pi/2} d\theta - 16a\int_0^{\pi/2} \cos 2\theta d\theta + 8a$$

$$\int_0^{\pi/2} \cos^2(2\theta) d\theta + 4\int_0^{\pi/2} \cos\theta d\theta - 4$$

$$\int_0^{\pi/2} \cos\theta\cos 2\theta d\theta - 4\int_0^{\pi/2} d\theta$$

$$= 8a\frac{\pi}{2} + 8a\int_0^{\pi/2} \cos^2(2\theta) d\theta + 4\sin\theta\Big|_\theta^{\pi/2} -$$

$$4\int_0^{\pi/2} \cos\theta\cos 2\theta - 4\frac{\pi}{2}$$

$$= a\left(4\pi + 8\int_0^{\pi/2} \cos^2(2\theta) d\theta\right) + 4 - 2\pi -$$

$$4\int_0^{\pi/2} \cos\theta\cos 2\theta d\theta$$

$$\int_0^{\pi/2} \cos^2(2\theta) d\theta = \frac{\theta}{2}\Big|_0^{\pi/2} + \frac{\sin 4\theta}{8}\Big|_0^{\pi/2}$$

$$= \frac{\pi}{4}$$

$$\int_0^{\pi/2} \cos 2\theta\cos\theta d\theta = \frac{\sin\theta}{2}\Big|_0^{\pi/2} + \frac{\sin 3\theta}{6}\Big|_0^{\pi/2}$$

$$= \frac{1}{2} + \frac{(-1)}{6}$$

$$= \frac{1}{3}$$

$$\frac{dF_1(a)}{da} = a \cdot 6\pi - 2\pi + \frac{8}{3}$$

-continued $$F_2(a) = \int_{\pi/2}^{\pi} [\cos^2\theta + |2a - 2a\cos 2\theta|^2 - 2\cos\theta(2a - 2a\cos 2\theta)]d\theta -$$
$$2\int_{\pi/2}^{\pi}(2a - \cos\theta - 2a\cos 2\theta)d\theta$$

$$\frac{dF_2(a)}{da} = \frac{\partial}{\partial a}\left[\int_{\pi/2}^{\pi}[4a^2 - 8a^2\cos 2\theta + 4a^2\cos^2(2\theta) -\right.$$
$$\left. 4a\cos\theta + 4a\cos\theta\cos 2\theta - 4a]d\theta\right]$$
$$= 8a\int_{\pi/2}^{\pi}d\theta - 16a\int_{\pi/2}^{\pi}\cos 2\theta d\theta + 8a\int_{\pi/2}^{\pi}\cos^2(2\theta)d\theta -$$
$$4\int_{\pi/2}^{\pi}\cos\theta d\theta + 4\int_{\pi/2}^{\pi}\cos\theta\cos(2\theta)d\theta - 4\int_{\pi/2}^{\pi}d\theta$$
$$= 8a\frac{\pi}{2} + 8a\int_{\pi/2}^{\pi}\cos^2(2\theta)d\theta - 4\sin\theta\Big|_{\pi/2}^{\pi} +$$
$$4\int_{\pi/2}^{\pi}\cos\theta\cos 2\theta d\theta - 4\frac{\pi}{2}$$

$$\int_{\pi/2}^{\pi}\cos^2 2\theta d\theta = \frac{\theta}{2}\Big|_{\pi/2}^{\pi} + \frac{\sin 4\theta}{8}\Big|_{\pi/2}^{\pi}$$
$$= \frac{\pi}{4}$$

$$\int_{\pi/2}^{\pi}\cos 2\theta\cos\theta d\theta = \frac{\sin\theta}{2}\Big|_{\pi/2}^{\pi} + \frac{\sin 3\theta}{6}\Big|_{\pi/2}^{\pi}$$
$$= -\frac{1}{2} + \frac{-(-1)}{6}$$
$$= -\frac{1}{3}$$

$$\frac{dF_2(2)}{da} = a(4\pi + 2\pi) + 4 - \frac{4}{3} - 2\pi$$

$$2\left(\frac{dF_1(a)}{da} + \frac{dF_2(a)}{da}\right) = 0 \Rightarrow 6\pi a$$
$$= 2\pi - \frac{8}{3} \Rightarrow a$$
$$= \frac{1}{3} - \frac{4}{9\pi}$$

As may be appreciated, a "least squares" (LS) criterion, F(a), is employed in the embodiment described herein, however this need not necessarily be the case. F(a) is further computed in terms of F1 and F2 for a<¼, relying on the symmetry of the cos function.

The basis for the same-smear filter typically is the following separable filter shape:

X coefficients:

| Re-sampling method | C0x | C1x | C2x |
|---|---|---|---|
| 0 <= dx <= 0.5 | a − 2a * dx | 1 − 2a − (1 − 4a) * dx | a + (1 − 2a) * dx |
| −0.5 <= dx <= 0 | a + (1 − 2a) * \|dx\| | 1 − 2a − (1 − 4a) * \|dx\| | a − 2a * \|dx\| |

Y coefficients:

| Re-sampling method | C0y | C1y | C2y |
|---|---|---|---|
| 0 <= dy <= 0.5 | a − 2a * dy | 1 − 2a − (1 − 4a) * dy | a + (1 − 2a) * dy |
| −0.5 <= dy <= 0 | a + (1 − 2a) * \|dy\| | 1 − 2a − (1 − 4a) * \|dy\| | a − 2a * \|dy\| |

The filter is a convolution of the two vectors above, as follows:

| | | |
|---|---|---|
| C0x * C0y | C1x * C0y | C2x * C0y |
| C0x * C1y | C1x * C1y | C2x * C1y |
| C0x * C2y | C1x * C2y | C2x * C2y |

Using a least squares optimization method for the 2 limiting cases (no translation at all and ½ pixel translations), an optimal coefficient has been devised:

a=⅓−4/(9*pi)=0.192

After a few iterations of frequency domain analysis, a suitable value for parameter a may be selected as a=0.15 or 0.192.

More generally, parameter a is determined by initially selecting a value, such as 0.192 or 0.15, and tuning the value, using an object whose defective locations are known, to suit the optical characteristics of the system so as to maximize the SNR (signal to noise ratio) of the defects relative to the artifactual noise generated by the imaging and inspection process.

It is appreciated that the re-sampling filter shown and described herein may be replaced by a similar filter with 4 or more coefficients rather than 3 coefficients as shown. A particular feature of a preferred embodiment of these filters is the ability to smear independent of the subpixel shift (dx,dy). Another particular feature of a preferred embodiment of these filters is the ability to smear independent of the subpixel component (dx,dy) of the shift performed on the image portion to be inspected in order to best align it to the corresponding portion of the reference image.

The term "cell to cell" refers to inspections in which the reference image used to inspect a particular cell within a particular die comprising a multiplicity of identical cells, is an identical cell within the same die. Typically, the reference image used in cell-to-cell applications comprises a median image generated from images of cells directly adjacent to the cell undergoing inspection. Cell-to-cell mode inspection in the current specification is described under the assumption that bright field illumination is used; however, it is appreciated that in fact dark field illumination may also be used in conjunction with cell-to-cell mode inspection.

Reference is now made to FIGS. 14A-14B which, taken together, are an image inspection method operative in accordance with a preferred embodiment of the present invention, and which is particularly suitable for performing cell-to-cell inspection of images of bright-field illuminated (or dark-field illuminated) objects. The methods shown and described herein are suitable for the inspection of microscopic objects generally, such as flat panel displays; however, the method is described herein, by way of example, in a context of inspection of wafers containing dies having repeating cells.

In step 810, generate at least 3 input images, including an original, first input image of a repetitively patterned object and at least two additional images of the repetitively patterned object, each translated one or a few cells away from the original input image in a particular direction. Use the same-smear filter of FIG. 13 on each of the at least three images including the original image, thereby to generate at least three same-smear aligned images.

Steps 820-870 here may be identical to steps 620-670 in FIG. 10A-10B.

Figure 15:
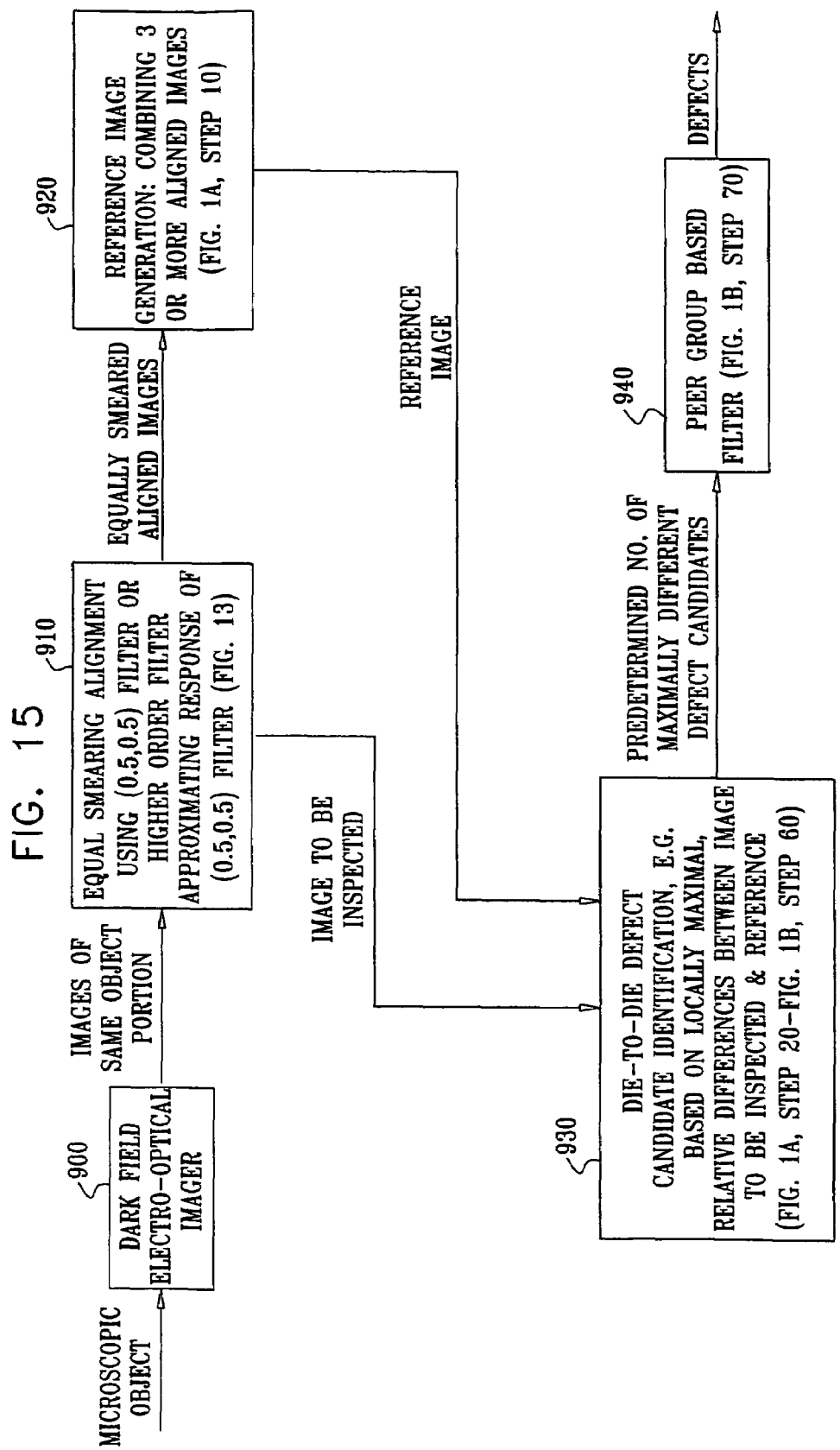
FIG. 15 is a simplified functional block diagram of a microscopic object die-to-die inspection system with peer-group filtering, constructed and operative in accordance with a first preferred embodiment of the present invention, and being particularly suitable for inspecting dark-field imaged microscopic objects.

FIG. 15 is a simplified functional block diagram of a microscopic object die-to-die inspection system with peer-group filtering, constructed and operative in accordance with a first preferred embodiment of the present invention, and being particularly suitable for inspecting dark-field imaged microscopic objects. As shown, an electro-optical imager 900 such as a Negevtech 302 wafer inspection tool, commercially available from Negevtech Ltd., 12 Hamada Street, Rehovot Israel 76703, operating in dark-field mode, generates a plurality of images of the same portion of a microscopic object to be inspected. The images are then mutually aligned, (image alignment unit 910), typically using the method of FIG. 13. The aligned images are combined into a reference image by reference image generation unit 920. A defect candidate identifier 930 is operative to compare the image to be inspected to the reference, on a die-to-die basis, based on identification of maximal differences between the image to be inspected and the reference, as described herein in detail with reference to FIGS. 1A-1B, steps 20-60. A predetermined number of maximally different defect candidates are preferably filtered, typically using the peer-group based filtering method described in FIG. 1B, step 70. The output of the peer group based filter 940 is a final list of defects.

Figure 16:
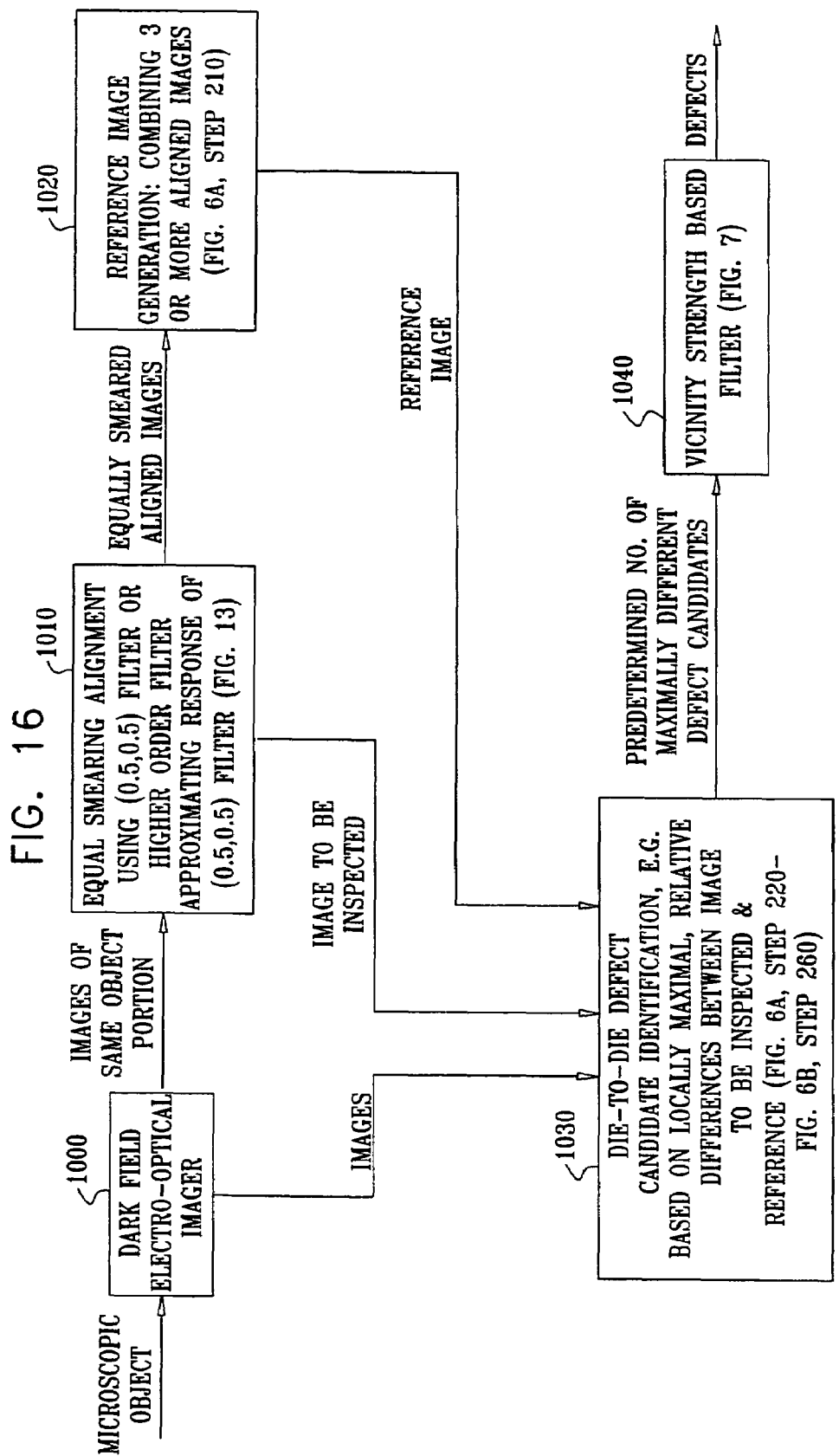
FIG. 16 is a simplified functional block diagram of a microscopic object die-to-die inspection system with vicinity strength based filtering, constructed and operative in accordance with a second preferred embodiment of the present invention, and being particularly suitable for inspecting dark-field imaged microscopic objects.

FIG. 16 is a simplified functional block diagram of a microscopic object die-to-die inspection system with vicinity based filtering, constructed and operative in accordance with a second preferred embodiment of the present invention, and being particularly suitable for inspecting dark-field imaged microscopic objects. As shown, an electro-optical imager 1000 such as a Negevtech 302 wafer inspection tool, commercially available from Negevtech Ltd., 12 Hamada Street, Rehovot Israel 76703, operating in dark-field mode, generates a plurality of images of the same portion of a microscopic object to be inspected. The images are then mutually aligned (image alignment unit 1010), typically using the method of FIG. 13. The aligned images are combined into a reference image by reference image generation unit 1020, typically as described in FIG. 6A, step 210. A defect candidate identifier 1030 is operative to compare the image to be inspected to the reference, on a die-to-die basis, based on identification of maximal differences between the image to be inspected and the reference, as described herein in detail with reference to FIGS. 6A-B, steps 220-260. A predetermined number of maximally different defect candidates are preferably filtered, typically using the peer based filtering method described in FIG. 7. The output of the vicinity strength based filter 1040 is a final list of defects.

Figure 17:
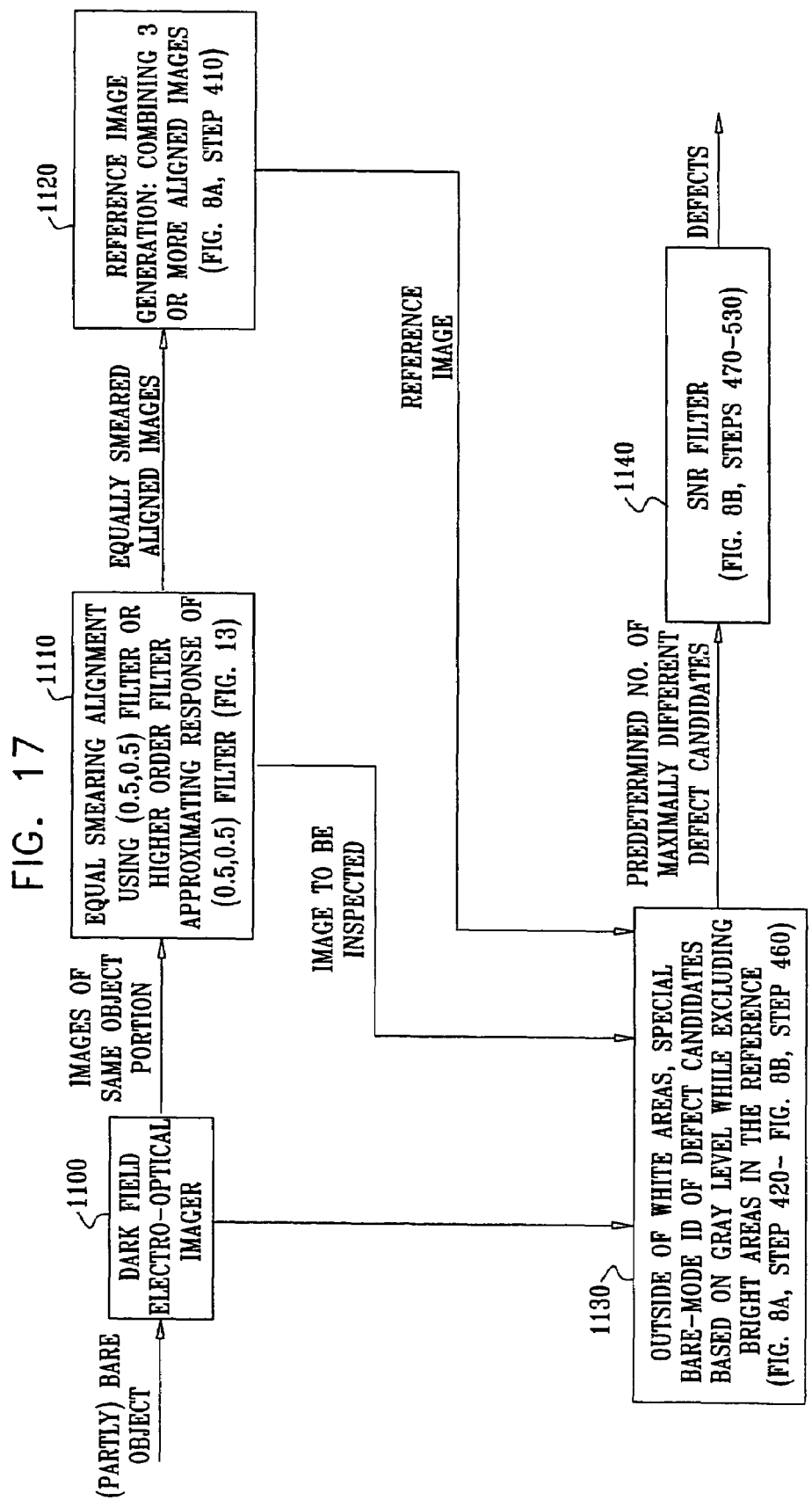
FIG. 17 is a simplified functional block diagram of a microscopic object die-to-die inspection system with peer-group filtering, constructed and operative in accordance with a third preferred embodiment of the present invention, and being particularly suitable for inspecting dark-field imaged microscopic objects having bare (i.e., substantially patternless) portions.

FIG. 17 is a simplified functional block diagram of a microscopic object die-to-die inspection system with peer-group filtering, constructed and operative in accordance with a third preferred embodiment of the present invention, and being particularly suitable for inspecting dark-field imaged microscopic objects having bare (i.e., substantially patternless) portions. As shown, an electro-optical imager 1100 such as a Negevtech 302 wafer inspection tool, commercially available from Negevtech Ltd., 12 Hamada Street, Rehovot Israel 76703, operating in dark-field mode, generates a plurality of images of the same portion of a microscopic object to be inspected. The images are then mutually aligned (image alignment unit 1110), typically using the method of FIG. 13. The aligned images are combined into a reference image by reference image generation unit 1120, typically as described in FIG. 8A, step 410. A defect candidate identifier 1130 is operative to compare the image to be inspected to the reference, on a die-to-die basis, based on comparison of gray levels, while excluding bright areas in the reference, as described herein in detail with reference to FIG. 8A, step 420-FIG. 8B, step 460. A predetermined number of maximally different defect candidates are preferably filtered, typically using the peer based filtering method described in FIG. 8B, steps 470-530. The output of the peer group based filter 1140 is a final list of defects.

Figure 18:
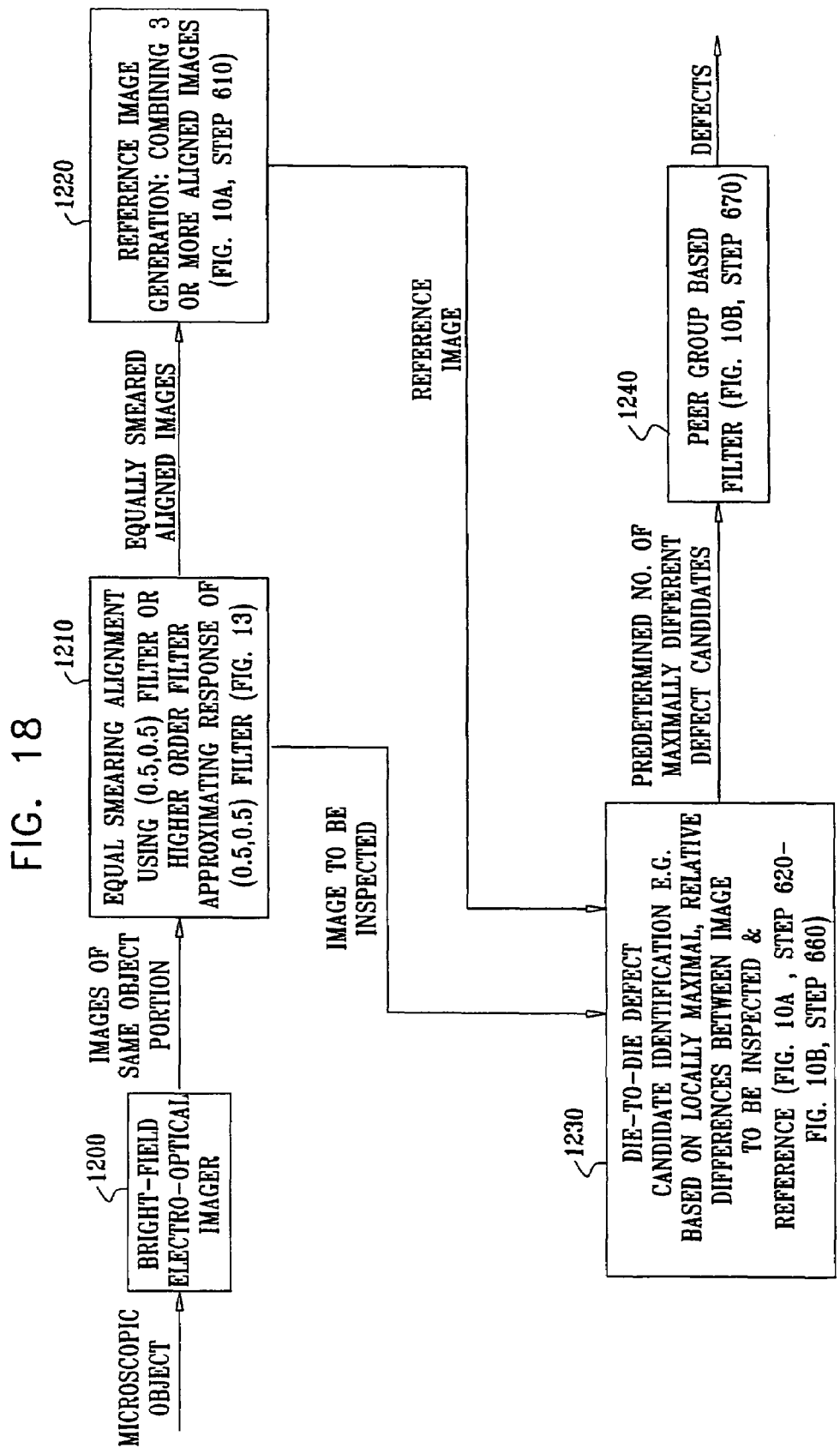
FIG. 18 is a simplified functional block diagram of a microscopic object die-to-die inspection system with peer-group filtering, constructed and operative in accordance with a fourth preferred embodiment of the present invention, and being particularly suitable for inspecting bright-field imaged microscopic objects.

FIG. 18 is a simplified functional block diagram of a microscopic object die-to-die inspection system with peer-group filtering, constructed and operative in accordance with a fourth preferred embodiment of the present invention, and being particularly suitable for inspecting bright-field imaged microscopic objects. As shown, an electro-optical imager 1200 such as a Negevtech 302 wafer inspection tool, commercially available from Negevtech Ltd., 12 Hamada Street, Rehovot Israel 76703,) operating in dark-field mode, generates a plurality of images of the same portion of a microscopic object to be inspected. The images are then mutually aligned (image alignment unit 1210), typically using the method of FIG. 13. The aligned images are combined into a reference image by reference image generation unit 1220, typically as described in FIG. 10A, step 610. A defect candidate identifier 1230 is operative to compare the image to be inspected to the reference, on a die-to-die basis, based on identification of maximal differences between the image to be inspected and the reference, as described herein in detail with reference to FIGS. 10A-10B, steps 620-660. A predetermined number of maximally different defect candidates are preferably filtered, typically using the peer-group based filtering method described in FIG. 10B, step 670. The output of the peer group based filter 1240 is a final list of defects.

Figure 19:
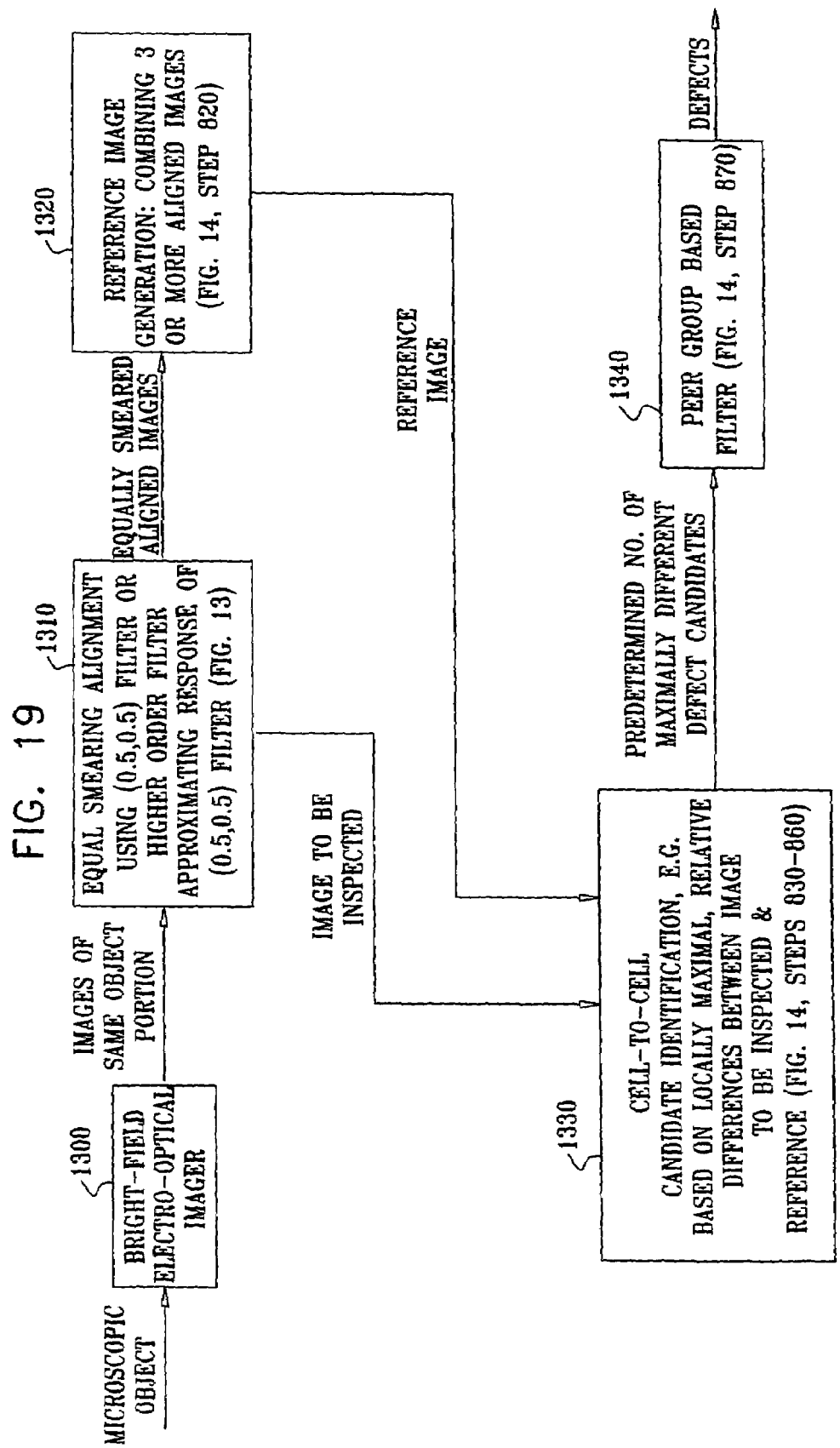
FIG. 19 is a simplified functional block diagram of a microscopic object cell-to-cell inspection system with peer-group filtering, constructed and operative in accordance with a fifth preferred embodiment of the present invention, and being particularly suitable for inspecting bright-field imaged microscopic objects.

FIG. 19 is a simplified functional block diagram of a microscopic object cell-to-cell inspection system with peer-group filtering, constructed and operative in accordance with a fifth preferred embodiment of the present invention, and being particularly suitable for inspecting bright-field imaged microscopic objects. As shown, an electro-optical imager 1300 such as a Negevtech 302 wafer inspection tool, commercially available from Negevtech Ltd., 12 Hamada Street, Rehovot Israel 76703, operating in dark-field mode, generates a plurality of images of the same portion of a microscopic object to be inspected. The images are then mutually aligned (image alignment unit 1310), typically using the method of FIG. 13. The aligned images are combined into a reference image by reference image generation unit 1320, typically as described in FIG. 13, step 788. A defect candidate identifier 1330 is operative to compare the image to be inspected to the reference, on a cell-to-cell basis, based on identification of maximal differences between the image to be inspected and the reference, as described herein in detail with reference to FIG. 14, steps 820-860. A predetermined number of maximally different defect candidates are preferably filtered, typically using the peer-group based filtering method described in FIG. 14, step 870. The output of the peer group based filter 1340 is a final list of defects.

It is appreciated that in accordance with a preferred embodiment of the present invention, several images (such as 3-4 images) of 3-4 respective repeating portions of an object are used to generate a combined reference image which is then used to inspect the 3-4 images. According to one variation, each of the images is inspected separately vis-a-vis the reference image. According to another variation, the several images are inspected simultaneously vis-a-vis the reference image, typically under the assumption that a pixel location is defective in, at most, one of the 3-4 images due to the relative rarity of defects. For simplicity, various embodiments of the present invention such as the dark field embodiment and the bright field embodiment, are described in terms of one or the other of the above variations. It is appreciated that this is not intended to be limiting and either variation may be employed to implement any of the various embodiments of the invention described herein.

It is appreciated that, according to a preferred embodiment of the present invention, all differences computed in accordance with the various embodiments of the invention are absolute differences.

According to various embodiments of the invention shown and described herein, candidate defects are re-examined and some candidate defects, which fall below a defined threshold, are discarded. The threshold, in vicinity-strength based filtering, may characterize the differences found within an entire vicinity of the defect's peak or, in peer-group based filtering, may be determined as a function of pixels which are "binned" together with the candidate defect. Pixels are binned together with the candidate defect if they and the candidate defect share similar gray level values in the reference image, according to one embodiment of the present invention described above, or if they and the candidate defect have similar difference values, for a particular pair of input images, according to another embodiment of the present invention. Preferably, the threshold values employed in any of the above embodiments need not be uniform over the entire area of the object to be inspected and instead may be varied by the user from one region of the object to another. The term "region" is used to denote a portion of the object to be inspected within which a uniform threshold value is used.

An alternative method of identifying pixels which are defect pixels, using n images of an object portion to be inspected, is as follows:

a. Generate n(n−1)/2 difference images by comparing each pair of images to one another, e.g. by pixel-by-pixel subtraction or by employing any other conventional comparison metric.

b. For each pixel location, compare the absolute difference image values in each of the difference images to one another, thereby to identify deviant values. For example, the (6,74) pixel value in each of five images 1, 2, 3, 4, and 5 may be as follows, respectively: 2, 4, 3, 16, 3. Comparing the difference values in difference images (1,2), (1,3), (1,4), (1,5), (2,3), (2,4), (2,5), (3,4), (3,5), (4,5) at pixel (6,74) may yield the following absolute difference values: 2, 1, 14, 1, 1, 12, 1, 13, 0, and 13. Comparing the highest value, 14, to the median value, 2, indicates that the highest value, 14, may be indicative of a defect at pixel (6,74) in image 1 or in image 4.

c. Typically, a decision is made as to whether the defect is in image 1 or image 4 by comparing the difference images in which image I is involved, collectively, to the difference images in which image 1 is not involved, and additionally comparing the difference images in which image 4 is involved, collectively, to the difference images in which image 4 is not involved, to determine which of the two images is more likely to contain the suspected defect.

It is appreciated that the software components of the present invention may, if desired, be implemented in ROM (read-only memory) form. The software components may, generally, be implemented in hardware, if desired, using conventional techniques.

It is appreciated that various features of the invention, which are, for clarity, described in the contexts of separate embodiments, may also be provided in combination in a single embodiment. Conversely, various features of the invention, which are, for brevity, described in the context of a single embodiment, may also be provided separately or in any suitable subcombination.

It will be appreciated by persons skilled in the art that the present invention is not limited to what has been particularly shown and described hereinabove. Rather, the scope of the present invention is defined only by the claims that follow:

The invention claimed is:

1. A method for inspecting a wafer including a multiplicity of dies, the method comprising in wafer inspection system, implementing the following steps:

aligning a plurality of images of the wafer, said plurality of images corresponding to a current image of the wafer, and generating from the aligned images of the wafer a reference image, said reference image having pixel values which are a median of pixel values of the plurality of aligned images at each pixel location within the aligned images;

generating a difference image according to a comparison of said current image of the wafer and said reference image;

sub-dividing the difference image into a plurality of sub-images each containing pixel locations corresponding to pixel locations within the reference image that fall within a range of gray level values; and for each respective sub-image, identifying a maximum difference pixel having a difference value larger than all other pixels in a respective sub-image, and generating therefrom a respective small current image for each respective sub-image;

determining, by comparing respective ones of the small current images with small reference images that include those pixels in the reference image which correspond in location to pixels included in the respective small current images, locations of possible defects in the wafer, the locations of possible defects identified by alarm pixels determined during the comparison;

filtering the alarm pixels to retain only those with relatively high difference values as compared to difference values of non-alarm pixels in each respective sub-image of the difference image to identify at least one defect candidate within each sub-image.

2. A method according to claim 1 and also comprising: dividing said sub-images into portions which it is desired to inspect separately; and for each portion, performing further defect detection analysis on a subset of defect candidates belonging to said portion, said subset comprising a predetermined number of those defect candidates within said portion which have the highest difference values.

3. A method according to claim 2 wherein said current image comprises patternless portions and wherein selecting defect candidates comprises selecting pixel within each respective sub-image with the largest gray level value.

4. A method according to claim 2 wherein said current image also comprises bright portions reflecting a large amount of light and wherein defect candidates are not selected within said bright portions.

5. A method according to claim 2 wherein said dividing step comprises dividing at least one of said sub-images into portions each having a defined gray level range in the reference image.

6. A method according to claim 2 wherein said dividing step comprises dividing at least one of said sub-images into portions each having a defined gray level range in a gradient of the reference image.

7. A method according to claim 2 wherein said dividing step comprises dividing at least one of said sub-images into portions, the portions having a defined gray level range in the difference image.

8. A method according to claim 1 wherein comparing respective ones of the small current images with the small reference images comprises generating, for each respective sub-image, a difference sub-image representing a difference between the respective sub-image and a portion of the reference image representing at least one identical sub-portion of the wafer and selecting at least one maximal difference value within said difference sub-image as a defect candidate.

9. A method according to claim 1 wherein further comprising identifying defect candidates which differ from their respectively corresponding locations in the reference image by more than a threshold value wherein said threshold value used for an individual defect candidate located at an individual location within said current image is a function of estimated noise between different images of said individual location.

10. A method according to claim 9 and also comprising estimating noise between the different images of said individual location by estimating noise, at each of a multiplicity of locations, between at least two different images of each such location.

11. A method according to claim 10 wherein said step of estimating noise also comprises estimating noise, at each of a multiplicity of similar locations, between the at least two different images of each such location.

12. A method according to claim 1 and wherein said each respective sub-image comprises at least a portion of a die which is being inspected.

13. A method according to claim 1 and wherein said comparing of respective ones of the small current images comprises identifying locations in the individual small current images which differ from the reference image by more than a threshold value, wherein said threshold value used for an individual location within each individual small current image is a function of estimated noise between different images of said individual location.

14. A method according to claim 1 and further comprising scoring said defect candidates and selecting a predetermined number of highest scoring defect candidates for further defect detection analysis.

15. A method according to claim 1 wherein generating said reference image comprises adding smear to at least one of said plurality of images of the wafer during said aligning so as to generate at least three images of said wafer having an essentially identical amounts of smear therein, and combining said at least three images having essentially identical amounts of smear, thereby to provide said reference image.

* * * * *